United States Patent
Schaberg et al.

(10) Patent No.: US 6,902,740 B2
(45) Date of Patent: Jun. 7, 2005

(54) PYRROLIDONOETHYL (METH)ACRYLATE CONTAINING PRESSURE SENSITIVE ADHESIVE COMPOSITIONS

(75) Inventors: Mark S. Schaberg, Lake Elmo, MN (US); Daniel C. Duan, St. Paul, MN (US); Kaveh Pournoor, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 50 days.

(21) Appl. No.: 09/901,219

(22) Filed: Jul. 9, 2001

(65) Prior Publication Data

US 2003/0113365 A1 Jun. 19, 2003

(51) Int. Cl.$^7$ .......................... A61F 13/02; A61F 13/00; A61L 15/16
(52) U.S. Cl. ...................... 424/448; 424/449; 424/443
(58) Field of Search ................... 424/448, 449, 424/443

(56) References Cited

U.S. PATENT DOCUMENTS

| | | | |
|---|---|---|---|
| 2,884,126 A | 4/1959 | Ulrich | 206/59 |
| RE24,906 E | 12/1960 | Ulrich | 206/59 |
| 3,966,902 A * | 6/1976 | Chromecek | 424/401 |
| 4,323,557 A | 4/1982 | Rosso et al. | 424/28 |
| 4,732,808 A * | 3/1988 | Krampe et al. | 424/448 |
| 4,968,562 A | 11/1990 | Delgado | 428/402 |
| 5,229,195 A | 7/1993 | Maruoka et al. | 428/220 |
| 5,252,395 A | 10/1993 | Maruoka et al. | 428/355 |
| 5,461,125 A | 10/1995 | Lu et al. | 525/293 |
| 5,573,778 A | 11/1996 | Therriault et al. | 424/448 |
| 5,580,647 A | 12/1996 | Larson et al. | 428/245 |
| 5,629,359 A | 5/1997 | Peeters et al. | 522/96 |
| 6,132,462 A * | 10/2000 | Li | 524/359 |
| 6,193,996 B1 * | 2/2001 | Effing et al. | 424/448 |
| 2002/0110585 A1 * | 8/2002 | Godbey et al. | 424/449 |

FOREIGN PATENT DOCUMENTS

| | | | |
|---|---|---|---|
| DE | 575327 | 4/1933 | 22/2 |
| DE | 2048312 | 4/1972 | C08G/20/10 |
| GB | 1101163 | 1/1968 | C08F/7/12 |
| GB | 1404989 | 3/1975 | C08F/222/16 |
| JP | 4-28705 | 1/1992 | C08F/20/36 |
| JP | 4028705 | 1/1992 | |
| WO | WO 96/08229 | * 3/1996 | |
| WO | WO 9837111 | 8/1998 | C08F/270/04 |

OTHER PUBLICATIONS

Database WPI—Section Ch, Week 199211, Derwent Publications, Ltd., London, GB; AN 1992–085280 XP002210904 & JP 04 028705 A Abstract.
"Acrylic Adhesives"—D. Satas, Handbook of Pressure Sensitive Adhesivo Technology, 2$^{nd}$ Ed., Van Nostrand Reinhold, New York, 1989, pp. 396–456.

* cited by examiner

Primary Examiner—Thurman K. Page
Assistant Examiner—Isis Ghali
(74) Attorney, Agent, or Firm—Robert W. Sprague

(57) ABSTRACT

The present invention relates to a pressure sensitive adhesive composition comprising a copolymer comprising pyrrolidonoethyl acrylate or pyrrolidonoethyl methacrylate. This composition may be used as part of a transdermal drug delivery device.

29 Claims, No Drawings

PYRROLIDONOETHYL (METH)ACRYLATE CONTAINING PRESSURE SENSITIVE ADHESIVE COMPOSITIONS

FIELD OF THE INVENTION

The present invention relates to a pressure sensitive adhesive composition comprising a copolymer comprising pyrrolidonoethyl acrylate or pyrrolidonoethyl methacrylate.

BACKGROUND OF THE INVENTION

Acrylic or acrylate copolymers are well known in the art and have been used commercially in pressure sensitive adhesive (PSA) compositions for about 50 years (see "Acrylic Adhesives", D. Satas, Handbook of Pressure Sensitive Adhesive Technology, 2nd Ed., Van Nostrand Reinhold, New York, 1989, pp. 396–456). It is well established that an acrylic copolymer suitable for use as a PSA must have two main characteristics that distinguish it from an acrylic copolymer that is not suitable for use as a PSA.

The first main characteristic of an acrylic copolymer suitable for use in a PSA is that the copolymer will contain a significant fraction of a monomer with a low glass transition temperature ($T_g$). This monomer will typically have a $T_g$ less than −20° C. and more preferably in the range of −40° C. to −80° C. It is this low $T_g$ monomer that gives the PSA its soft, tacky properties.

The second main characteristic of an acrylic copolymer suitable for use in a PSA is a means of providing reinforcement to the PSA. This reinforcement prevents the PSA from splitting and oozing during use. There are a number of methods for providing this reinforcement, including for example: addition of high $T_g$ monomers to the copolymer; addition of monomers that cause inter-molecular interactions between individual copolymers; covalent crosslinking of the copolymer; and physical crosslinking of the copolymer via graft or block copolymers.

The first, or tacky, characteristic of an acrylic copolymer was described as early as 1933 in German Patent No. 575,327 (Bauer). The reinforcing feature necessary for a suitable acrylic copolymer PSA, however, was not described until 1959 in U.S. Pat. No. 2,884,126 (Ulrich) later reissued as U.S. Pat. No. RE 24,906. This was the first disclosure of the concept of incorporating high $T_g$ functional monomers into the acrylic copolymer for reinforcement, and these monomers, such as acrylic acid and acrylamide, continue to be used widely today for this purpose.

Another effect, however, of incorporating functional monomers into a copolymer is to change the average chemical properties of the copolymer. The chemical properties can affect many performance characteristics of the PSA, such as the ability of a PSA to wet a surface, the ability of a PSA to dissolve or complex additives, and the relative stability of both the PSA and any additives included with the PSA.

In particular, functional monomers can have significant effects on dissolving or complexing small molecule additives. An example of this effect on a PSA is the interaction of iodine with N-vinyl pyrrolidone described in U.S. Pat. No. 4,323,557 (Rosso et. al.). A disadvantage, however, to the general concept of incorporation of functional monomers for adjusting chemical properties is that the functional monomers can also have a strong effect on the physical properties of the copolymer (e.g., reinforcement). Thus the amount of functional monomer that may be incorporated is typically quite limited, since excessive reinforcement will cause a loss of the soft, tacky properties necessary in a PSA.

SUMMARY OF THE INVENTION

The present invention provides a pressure sensitive adhesive composition comprising a copolymer comprising (a) at least one A monomer selected from the group consisting of an alkyl acrylate containing 4 to 12 carbon atoms in the alkyl group and an alkyl methacrylate containing 4 to 12 carbon atoms in the alkyl group; and (b) at least one pyrrolidone monomer selected from the group consisting of pyrrolidonoethyl acrylate and pyrrolidonoethyl methacrylate.

In a preferred embodiment this pressure sensitive adhesive composition may be combined with a drug to provide a transdermal drug delivery composition.

These compositions may be combined with a backing to create pressure sensitive tapes, which in a preferred embodiment will be transdermal drug delivery devices.

The present invention also provides a method for transdermal delivery of a drug comprising the steps of (A) a step of providing a composition comprising
 (i) a copolymer comprising
  (a) at least one A monomer selected from the group consisting of an alkyl acrylate containing 4 to 12 carbon atoms in the alkyl group and an alkyl methacrylate containing 4 to 12 carbon atoms in the alkyl group; and
  (b) at least one pyrrolidone monomer selected from the group consisting of pyrrolidonoethyl acrylate and pyrrolidonoethyl methacrylate; and
 (ii) a drug in an amount such that the composition delivers a therapeutically effective amount for the indication being treated; and (B) a step of applying the composition to an external part of the human body for a period sufficient to achieve the desired therapeutic result Pyrrolidonoethyl acrylate and pyrrolidonoethyl methacrylate are functional monomers that may be incorporated into an acrylic copolymer in significant amounts for adjusting chemical properties without causing large changes in physical properties that occur with typical functional monomers. The chemical structure of one of the segments of the copolymer is shown below in FIG. 1. This provides the useful benefit of allowing adjustment of chemical properties of the copolymer without causing undesirable changes in the PSA properties. The ability to increase the solubility of a drug in the acrylic copolymer (when compared to a like copolymer not containing pyrrolidonoethyl (meth)acrylate) without causing excessive reinforcement and loss of PSA properties is a preferred benefit gained by incorporation of pyrrolidonoethyl (meth)acrylate in the copolymer.

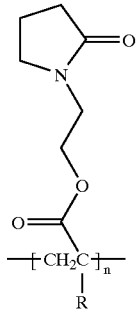

FIG. 1

R = H, pyrrolidonoethyl acrylate
R = CH₃, pyrrolidonoethyl methacrylate

DETAILED DESCRIPTION OF THE INVENTION

The composition of the present invention comprises a copolymer of alkyl (meth)acrylate A monomers in which the alkyl group has 4 to 12 carbon atoms and at least one pyrrolidone monomer selected from the group consisting of pyrrolidonoethyl acrylate (N-(acryloyloxyethyl)pyrrolidin-2-one) and pyrrolidonoethyl methacrylate (N-(methacryloyloxyethyl)pyrrolidin-2-one) and devices containing these compositions.

Suitable acrylic copolymers for use in the composition preferably comprise about 40 to about 95 percent by weight, more preferably 50 to 70 percent by weight, based on the total weight of all monomers in the copolymer, of one or more A monomers selected from the group consisting of alkyl acrylates containing 4 to 12 carbon atoms in the alkyl group and alkyl methacrylates containing 4 to 12 carbon atoms in the alkyl group. Examples of suitable alkyl acrylates and methacrylates include n-butyl, n-pentyl, n-hexyl, isoheptyl, n-nonyl, n-decyl, isohexyl, 2-ethyloctyl, isooctyl and 2-ethylhexyl acrylates and methacrylates. Preferred alkyl acrylates include isooctyl acrylate, 2-ethylhexyl acrylate, n-butyl acrylate, and cyclohexyl acrylate. Isooctyl acrylate is a particularly preferred A monomer.

The preferred acrylic copolymer further comprises about 5 to about 55 percent by weight, more preferably about 10 to about 45 percent by weight, based on the total weight of all monomers in the copolymer, of one or more pyrrolidone monomers selected from the group consisting of pyrrolidonoethyl acrylate and pyrrolidonoethyl methacrylate. Pyrrolidonoethyl acrylate is a particularly preferred pyrrolidone monomer.

The copolymer may optionally further comprise about 5 to about 40 percent by weight, more preferably about 10 to about 30 percent by weight, based on the total weight of all monomers in the copolymer of one or more B monomers that are copolymerizable with the A and pyrrolidone monomers. Suitable B monomers include those containing a functional group selected from the group consisting of carboxylic acid, sulfonamide, urea, carbamate, carboxamide, hydroxy, amino, oxy, oxo, and cyano. Exemplary B monomers include acrylic acid, methacrylic acid, maleic acid, a hydroxyalkyl acrylate containing 2 to 4 carbon atoms in the hydroxyalkyl group, a hydroxyalkyl methacrylate containing 2 to 4 carbon atoms in the hydroxyalkyl group, acrylamide, methacrylamide, an alkyl substituted acrylamide containing 1 to 8 carbon atoms in the alkyl group, N-vinyl-N-methyl acetarnide, N-vinyl valerolactam, N-vinyl caprolactam, N-vinyl-2-pyrrolidone, glycidyl methacrylate, vinyl acetate, alkoxyethyl acrylate containing 1 to 4 carbon atoms in the alkoxy group, alkoxyethyl methacrylate containing 1 to 4 carbon atoms in the alkoxy group, 2-ethoxyethoxyethyl acrylate, furfuryl acrylate, furfuryl methacrylate, tetrahydrofurfuryl acrylate, tetrahydrofurfuryl methacrylate, propylene glycol monomethacrylate, propylene oxide methyl ether acrylate, di(lower)alkylamino ethyl acrylate, di(lower)alkylamino ethyl methacrylate, di(lower alkyl)aminopropyl methacrylamide, acrylonitrile, methyl acrylate, and methacrylonitrile. Preferred B monomers include acrylic acid, methyl acrylate, and vinyl acetate.

The copolymer may optionally further comprise a substantially linear macromonomer copolymerizable with the A and pyrrolidone monomers and having a weight average molecular weight in the range of about 500 to about 500,000, preferably about 2,000 to about 100,000 and more preferably about 4,000 to about 20,000. The macromonomer, when used, is generally present in an amount of not more than about 20% and preferably not more than about 10% by weight based on the total weight of all monomers in the copolymer. Suitable macromonomers include functionally terminated polymethylmethacrylate, styrene/acrylonitrile, polyether, and polystyrene macromonomers. Examples of useful macromonomers and their preparation are described in Krampe et al., U.S. Pat. No. 4,693,776, the disclosure of which is incorporated herein by reference. Polymethylmethacrylate macromonomers are particularly preferred.

Preferred copolymers are themselves pressure sensitive adhesives.

In a preferred embodiment, the composition may further comprise a drug. The drug will be present in an amount such that the composition delivers a therapeutically effective amount for the indication being treated. This amount will vary according to the type of drug used, the condition to be treated, the amount of time the composition is allowed to remain in contact with the skin of the subject, and other factors known to those of skill in the art. However, the amount of drug present in the transdermal drug delivery composition of the invention will generally be about 0.01 to 40 wt-%, preferably about 1.0 to 20 wt-%, based on the total weight of the composition. In a composition of the invention the drug is dispersed, preferably homogeneously, and more preferably dissolved in the pressure sensitive adhesive.

Any drug that is suitable for transdermal delivery may be used in the transdermal drug delivery composition of the invention. Examples of useful drugs include, but are not limited to, antiinflammatory drugs, both steroidal (e.g., hydrocortisone, prednisolone, triamcinolone) and nonsteroidal (e.g., naproxen, piroxicam); antibacterials (e.g., penicillins such as penicillin V, cephalosporins such as cephalexin, erythromycin, tetracycline, gentamycin, sulfathiazole, nitrofurantoin, and quinolones such as norfloxacin, flumequine, and ibafloxacin); antiprotozoals (e.g., metronidazole); antifungals (e.g., nystatin); coronary vasodilators (e.g., nitroglycerin); calcium channel blockers (e.g., nifedipine, diltiazem); bronchodilators (e.g., theophylline, pirbuterol, salmeterol, isoproterenol); enzyme inhibitors such as collagenase inhibitors, protease inhibitors, elastase inhibitors, lipoxygenase inhibitors (e.g., zileuton), and angiotensin converting enzyme inhibitors (e.g., captopril, lisinopril); other antihypertensives (e.g., propranolol); leukotriene antagonists; anti-ulceratives such as H2 antagonists; steroidal hormones (e.g., progesterone, testosterone, estradiol); antivirals and/or immunomodulators (e.g., 1-isobutyl-1H-imidazo[4,5-c]quinolin-4-amine, 1-(2-hydroxy-2-methylpropyl)-1H-imidazo[4,5-c]quinoline-4-amine, and other compounds disclosed in U.S. Pat. No. 4,689,338, incorporated herein by reference, acyclovir); local anesthetics (e.g., benzocaine, propofol); cardiotonics (e.g., digitalis, digoxin); antitussives (e.g., codeine, dextromethorphan); antihistamines (e.g., diphenhydramine, chlorpheniramine, terfenadine); narcotic analgesics (e.g., morphine, fentanyl); peptide hormones (e.g., human or animal growth hormones, LHRH); sex hormones (e.g., estrogens, testosterone, progestins such as levonorgestrel, norethindrone, gestodene); cardioactive products such as atriopeptides; proteinaceous products (e.g., insulin); enzymes (e.g., anti-plaque enzymes, lysozyme, dextranase); antinauseants (e.g., scopolomine); anticonvulsants (e.g., carbamazine); immunosuppressives (e.g., cyclosporine); psychotherapeutics (e.g., diazepam); sedatives (e.g., phenobarbital); anticoagulants (e.g., heparin); analgesics (e.g., acetaminophen); antimigraine agents (e.g., ergotamine, melatonin, sumatriptan); antiarrhythmic agents (e.g., flecainide); antiemetics (e.g., metaclopromide, ondansetron); anticancer agents (e.g., methotrexate); neurologic agents such as anxiolytic drugs; hemostatics; anti-obesity agents; and the like, as well as pharmaceutically acceptable salts and esters thereof. Preferred drugs include atenolol and fentanyl.

In another preferred embodiment, the composition may further comprise an anti-microbial agent. The antimicrobial agent may be any broad spectrum antimicrobial agent that is suitable for topical application. Examples of suitable antimicrobial agents are iodine, including iodine complexes with sodium or potassium iodide as well as polymeric complexes often called iodophors such as povidone-iodine and polyethylene glycol complexes, hexylresorcinol, chlorhexidine or a suitable salt thereof such as chlorhexidine gluconate or chlorhexidine acetate, triclosan, p-chloro m-xylenol (PCMX), phenols, peroxides, silver and silver salts such as silver chloride, silver oxide and silver sulfadiazine, long chain alkyl quaternary ammonium compounds, and mono C8–C12 alkyl esters of glycerin and propylene glycol. Antifungal agents may also be incorporated and include any of the "azoles" such as miconazole nitrate, chlortrimazole, econazole, ketoconizole and the like as well as tolnaftate and undecylic acid and its salts. Iodine, iodine complexes with sodium or potassium iodide, povidone-iodine, and chlorhexidine are preferred antimicrobial agents. The antimicrobial agent is present in these compositions in an effective amount (i.e., an amount that provides for release of the antimicrobial agent from the compositions substantially continuously over a sustained period of time such as about 30 minutes). For example, when the antimicrobial agent is chlorhexidine or a derivative thereof, the composition will preferably contain the antimicrobial agent in an amount by weight of about 1 to 10% based on the total weight of the composition.

The composition may further comprise a softening agent. Suitable softening agents (softeners) include certain pharmaceutically acceptable materials that have been used as skin penetration enhancers or solubilizers in transdermal drug delivery systems. Exemplary materials include $C_8$–$C_{36}$ fatty acids such as isostearic acid, octanoic acid, and oleic acid; $C_8$–$C_{36}$ fatty alcohols such as oleyl alcohol and lauryl alcohol; lower alkyl esters of $C_8$–$C_{36}$ fatty acids such as ethyl oleate, isopropyl myristate, butyl stearate, and methyl laurate; di(lower) alkyl esters of $C_6$–$C_8$ diacids such as diisopropyl adipate; monoglycerides of $C_8$–$C_{36}$ fatty acids such as glyceryl monolaurate; tetraglycol (tetrahydrofurfuryl alcohol polyethylene glycol ether); tetraethylene glycol (ethanol,2,2'-(oxybis(ethylenoxy)) diglycol); $C_6$–$C_{36}$ alkyl pyrrolidone carboxylates; polyethylene glycol; propylene glycol; 2-(2-ethoxyethoxy)ethanol; diethylene glycol monomethyl ether; N,N-dimethyldodecylamine-N-oxide and combinations of the foregoing. Alkylaryl ethers of polyethylene oxide, polyethylene oxide monomethyl ethers, and polyethylene oxide dimethyl ethers are also suitable, as are solubilizers such as glycerol and N-methyl pyrrolidone. The terpenes are another useful class of softeners, including pinene, d-limonene, carene, terpineol, terpinen-4-ol, carveol, carvone, pulegone, piperitone, menthone, menthol, neomenthol, thymol, camphor, borneol, citral, ionone, and cineole, alone or in any combination. Of the terpenes, terpineol, particularly α-terpineol, is preferred.

Preferred softeners include glyceryl monolaurate, terpineol, lauryl alcohol, tetraglycol, tetraethylene glycol, propylene glycol, isopropyl myristate, ethyl oleate, methyl laurate, and 2-(2-ethoxyethoxy)ethanol.

While many of the softeners enumerated above are known to affect skin penetration rate, certain softeners affect aspects of performance other than and in addition to skin penetration rate. For example, they are useful in softening or increasing the compliance value and/or lowering the glass transition temperature of copolymers, such that the resulting composition is more suitable for use as a pressure sensitive adhesive.

In a composition of the invention the softener(s) is dispersed, preferably substantially uniformly, and more preferably dissolved in the composition. Where the softener is a penetration enhancer, it is present in an amount that enhances drug permeation through the skin compared to a like composition not containing the penetration enhancer(s) when this phenomenon is measured using the skin penetration model described below. The total amount of softener will generally be about 5 to about 40% by weight based on the total weight of the composition.

The copolymers described above can be prepared by methods well known to those skilled in the art and described for example in U.S. Pat. No. RE 24,906 (Ulrich), U.S. Pat. No. 4,732,808 (Krampe et. al.), and International Publication Number WO 96/08229 (Garbe et. al.), the disclosures of which are incorporated herein by reference.

Another copolymerization method is photopolymerization of the monomer mixture initiated by ultraviolet (UV) radiation. This monomer mixture, along with a suitable photoinitiator, is coated onto a flexible carrier web and polymerized in an inert (i.e., oxygen free) atmosphere. A sufficiently inert atmosphere can be achieved by covering a layer of the photoactive coating with a plastic film which is substantially transparent to UV radiation, and irradiating through that film using fluorescent-type UV lamps.

Other solventless polymerization methods, such as the continuous free radical polymerization method described in U.S. Pat. Nos. 4,619,979 (Barber et. al.) and 4,843,134 (Barber et. al.); the essentially adiabatic polymerization methods using a batch reactor described in U.S. Pat. No. 5,637,646 (Ellis); and, the methods described for polymerizing packaged polymerizable mixtures described in U.S. Pat. No. 5,804,610 (Hamer et. al.) may also be utilized to prepare the copolymers and pressure sensitive adhesive compositions of the present invention.

The pressure sensitive adhesive copolymer compositions prepared in accordance with the present invention are easily coated upon suitable flexible or inflexible backing materials by conventional coating techniques, such as roll coating, spray coating, curtain coating, and the like to produce coated pressure sensitive adhesive sheet materials in accord with the present invention. The PSA compositions may also be coated without modification by extrusion coating, coextrusion, hot-melt coating and the like by employing suitable conventional coating devices for this purpose.

The PSA compositions may also be coated using conventional methods for preparing melt-blown fibers, such as described in U.S. Pat. No. 6,083,856 (Joseph, et. al). Such acrylate-based pressure-sensitive adhesive fibers typically have a diameter of no greater than about 100 μm and are useful in making coherent nonwoven webs that can be used in making a wide variety of products. Preferably, such fibers have a diameter of no greater than about 50 μm, and often, no greater than about 25 μm. Fibers of no greater than about 50 μm are often referred to as "microfibers."

The flexible backing material may be any material conventionally utilized as a tape backing or any other flexible material. Typical examples of flexible backing materials employed as conventional tape backings which may be useful for the pressure sensitive adhesive compositions of the present invention include those made of paper, plastic films such as polypropylene, polyethylene, particularly low density polyethylene, linear low density polyethylene, metallocene polyethylenes, high density polyethylene, polyvinyl chloride, polyester (e.g., polyethylene terephthalate), ethylene-vinyl acetate copolymer, polyurethane, cellulose acetate and ethyl cellulose. Backings that are layered such as polyethylene terephthalate-aluminum-polyethylene composites are also suitable.

Backings may also be prepared of fabric such as woven fabric formed of threads of synthetic or natural materials such as cotton, nylon, rayon, glass, ceramic material, and the like or nonwoven fabric such as air laid webs of natural or synthetic fibers or blends of these. The backing may also be formed of metal, metalized polymeric films, or ceramic sheet materials.

The coated sheet materials may take the form of any article conventionally known to be utilized with PSA compositions such as labels, tapes, signs, covers, marking indicia, and the like.

Appropriate PSA properties will vary depending on the desired end use. In order to achieve these appropriate PSA properties, it should be noted that the amount and structure of the comonomers in the copolymer, the inherent viscosity of the copolymer, the amount and type of any optional additives, and any optional crosslinking can be selected to obtain desired properties. The inherent viscosity of the copolymer is such as to ultimately provide a suitable pressure sensitive adhesive when used in a composition or device of the invention. Preferably the copolymer has an inherent viscosity in the range of about 0.2 dL/g to about 2.0 dL/g, more preferably about 0.5 dL/g to about 1.4 dL/g.

In a preferred embodiment of the invention, the pressure sensitive adhesive composition is used in a transdermal drug delivery device. Backings for such a device are flexible such that the device conforms to the skin. Examples of suitable backing materials are described above. The backing should be substantially inert to the components of the composition.

Transdermal drug delivery devices of the invention are preferably prepared by combining the copolymer, drug, and optional softener with an organic solvent (e.g., ethyl acetate, isopropanol, methanol, acetone, 2-butanone, ethanol, toluene, alkanes, and mixtures thereof) to provide a coating composition. The mixture is shaken or stirred until a homogeneous coating composition is obtained. The resulting composition is then applied to a release liner using conventional coating methods (e.g., knife coating or extrusion die coating) to provide a predetermined uniform thickness of coating composition. Suitable release liners include conventional release liners comprising a known sheet material such as a polyester web, a polyethylene web, a polystyrene web, or a polyethylene-coated paper coated with a suitable fluoropolymer or silicone based coating. The release liner that has been coated with the composition is then dried and laminated onto a backing using conventional methods.

The transdermal drug delivery devices of the invention can be made in the form of an article such as a tape, a patch, a sheet, a dressing or any other form known to those skilled in the art. Generally, the device will be in the form of a patch of a size suitable to deliver a preselected amount of drug through the skin. Generally, the device will have a surface area of about 5 cm$^2$ to about 100 cm$^2$ and preferably about 10 cm$^2$ to about 40 cm$^2$.

The physical properties desirable in a transdermal drug delivery device are well known to those skilled in the art. For example, it is desirable to have sufficiently little cold flow that a device of the invention is stable to flow upon storage. It is also preferred that it adheres well to the skin and release cleanly from the skin. The amount and structure of the comonomers in the copolymer, the inherent viscosity of the copolymer, and the amount and type of softeners are selected in order to achieve resistance to cold flow, preferred levels of skin adhesion and clean release, such that the pressure sensitive adhesive layers obtain the desired balance of these properties.

The following examples are provided to further illustrate the invention, but are not intended to limit the invention in any way. In the examples below all percentages and ratios are weight/weight unless otherwise indicated. The copolymer ratios are based on the charge ratios used in the polymer synthesis. Unless otherwise indicated, the weight percent of drug and/or softener in a particular composition is based on the amount used in preparing the coating formulation and assumes that none is lost during the drying step. The abbreviations IOA, MA, PMMAMac, PyEA, and VOAc are used for isooctyl acrylate, methyl acrylate, polymethyl methacrylate macromonomer, pyrrolidonoethyl acrylate, and vinyl acetate respectively. The polymethyl methacrylate macromonomer used was ELVACITE™ 1010 from ICI Acrylics.

EXAMPLES

Shear Creep Compliance Test Method

The compliance values given in the examples below were obtained using a modified version of the Creep Compliance Procedure described in U.S. Pat. No. 4,737,559 (Kellen). The release liner is removed from a sample of the material to be tested. The exposed surface is folded back on itself in the lengthwise direction to produce a "sandwich" configuration (i.e., backing/pressure sensitive adhesive/backing). The sandwich sample is passed through a laminator. Two test samples of equal area are cut from the laminated sandwich using a die. One test sample is centered on the stationary plate of a shear-creep rheometer. The small, non-stationary plate of the shear-creep rheometer is centered over the first sample on the stationary plate such that the hook is facing up and toward the front of the rheometer. The second test sample is centered on the upper surface of the small, non-stationary plate. The large non-stationary plate is placed over the second test sample and the entire assembly is clamped into place. A string is connected to the hook of the small, non-stationary plate and extended over the front pulley of the rheometer. A weight (e.g., 500 g) is attached to the free end of the string and supported so as not to place a load on the non-stationary plate. The support for the weight is removed to allow it to hang freely. The weight exerts a load on the non-stationary plate and the displacement of the non-stationary plate is recorded as a function of time. The weight is removed after exactly 3 minutes have elapsed. The shear creep compliance is then calculated using the equation:

$$J = 2\frac{AX}{hf}$$

where A is the area of one face of the test sample, h is the thickness of the pressure sensitive adhesive mass (i.e., two times the thickness of the pressure sensitive adhesive layer on each sandwich), X is the displacement and f is the force due to the mass attached to the string. Where A is expressed in cm$^2$, h in cm, X in cm and f in dynes, the compliance value is given in cm$^2$/dyne.

Tack Test Method

The tack values reported in the examples below were obtained using a Digital Polyken Probe Tack Tester, Model 80-02-01 (Testing Machines, Inc., Amityville, N.Y.). The machine settings are as follows: speed: 0.5 cm/second; dwell: 2 seconds; mode: peak. A stainless steel probe is used. The result of the test is the force required to break the bond between the probe and the surface of the test sample. The force is measured in "grams of tack". Unless otherwise indicated, each reported value is the average of 5 independent determinations.

Adhesion to Steel Test Method—A

The adhesion to steel values given in the examples below were obtained using the following test method, unless noted in the example. The test was based on ASTM D3330-90, which describes peel from a substrate at a 180° peel angle done with a constant-rate-of-extension tensile tester.

A 1.0 cm wide strip is cut from the laminate to be tested. A portion of the release liner is removed to expose some of the pressure sensitive adhesive. A leader (a piece of polyester film at least 1.0 cm long and approximately 15.2 cm long) is firmly adhered to a 0.3 to 0.6 cm length of the exposed pressure sensitive adhesive. The rest of the release liner is removed. The test specimen is positioned pressure sensitive adhesive side down, lengthwise with and approximately in the center of a clean stainless steel plate (The surface of the plate is washed thoroughly once with methyl ethyl ketone and twice with n-heptane.). The test specimen is rolled once in each direction with a 2.0 kg roller.

The end of the stainless steel plate from which the leader strip extends is clamped into the lower jaw of a tensile tester. The free end of the leader strip is doubled back so that the angle of removal will be 180° and clamped into the upper jaw of the tensile tester so that there is no slack in the leader.

The test specimen is peeled away from the plate at a rate of 6 inches/minute (15.2 cm/minute). The results are reported in g/cm.

Adhesion to Steel Test Method—B

The test was performed as described above in the Adhesion to Steel Test Method—A, except as noted below. A 2.54 cm wide strip is cut from the laminate for testing. The stainless steel plate was washed with a 50/50 n-heptane/isopropanol v:v solution. The test specimen is rolled once in each direction with a 3.492 cm (1.375 inch) diameter, 159.24 gram roller. The results are reported in g/2.54 cm.

Adhesion to VITRO-SKIN™ Test Method

The adhesion to Vitro-Skin values given in the examples below were obtained using the following test method. The test was based on ASTM D3330-90, which describes peel from a substrate at a 180° peel angle done with a constant-rate-of-extension tensile tester.

A solution of glycerol/water 30/70 v/v is poured into a hydration chamber to provide a layer approximately 1.2 cm deep. A rack is positioned in the hydration chamber such that it is level and the upper surface of the rack is above the surface of the liquid. VITRO-SKIN™ substrate (N-19 designed to mimic human back skin; available from Innovative Measurement Solutions, Inc., Milford, Conn., USA) is cut smooth side up into 3.2 cm by 8.9 cm strips. The strips are placed smooth side up in a single layer on the rack in the hydration chamber. The chamber is sealed then placed in the constant temperature (23°) and humidity (50% relative humidity) room where the tensile tester is also located. The strips are allowed to condition for at least 24 hours.

The surface of a stainless steel plate is laminated with a layer of 40 mil (1016 µm) foam tape cut to the same size as the plate. A piece of double-stick tape cut the same size as the Vitro-Skin substrate strip is laminated to the center of the foam layer.

The laminate to be tested is cut into 2.5 cm by 10 cm strips. A 15 cm leader strip is attached about 0.6 cm from the end of the test specimen. A strip of Vitro-Skin substrate is removed from the hydration chamber and immediately placed rough side facing up onto the exposed surface of the double-stick tape on the stainless steel plate. The Vitro-Skin substrate is slowly (~30 cm/min) rolled down once with a 2.0 kg hand roller. The test specimen is centered over the substrate then applied to the substrate with the release liner being removed as the specimen is applied. The test specimen is slowly (~30 cm/min) rolled down once with a 2.0 kg hand roller.

The end of the stainless steel plate from which the leader strip extends is clamped into the lower jaw of a tensile tester. The free end of the leader strip is doubled back so that the angle of removal will be 180° and clamped into the upper jaw of the tensile tester so that there is no slack in the leader.

After 2 minutes of dwell time the test specimen is peeled away from the Vitro-Skin substrate at a rate of 15.2 cm/minute. The results are reported in g/cm. Each strip of Vitro-Skin substrate is used only once.

Skin Panel Test Methods

The skin panel data given in the examples below was obtained using the following test methods.

Skin Adhesion Test

Adhesion to skin is determined on human volunteers. The laminates to be tested are cut into 1.3 cm by 7.6 cm strips with rounded corners. The strips are applied to the backs of a selected number, usually five or six, of volunteers. During application and removal of the test strips, the volunteers lay in a prone position with their arms at their sides and their heads turned to one side. For each individual, two or three strips of each specimen are applied to both sides of the spinal column with the length of each strip positioned at a right angle to the spinal column. The test strips are applied without tension or pulling of the skin. The strips are pressed into place with a single pass of a 2.0 kg roller.

The test strips are then removed either immediately ($T_0$) or after 24 ($T_{24}$) or 72 hours ($T_{72}$) of continuous contact with the skin. The strips are removed at a removal angle of 180° and at a removal rate of 15 cm/min using a conventional adhesion tester having a test line and a clip attached to the test line. The clip is attached to the edge of the strip that is farthest from the spinal column by manually lifting about 1 cm of the strip from the skin and attaching the clip to the raised edge. The adhesion tester is aligned with and at the same height as the strip to be removed. An example of a suitable adhesion tester for use in this test comprises a strain gauge mounted on a motor driven carriage.

The measured force required to remove the test strip is reported in g/cm.

Pressure Sensitive Adhesive Lift Test

The Pressure Sensitive Adhesive List Test is a subjective assessment of the extent to which a test strip prematurely separates from the body after application in accordance with the Skin Adhesion Test. The test strips are visually inspected just prior to testing for skin adhesion at 24 hours and 72 hours to determine the extent to which the edges of the test strip have separated from the skin. Each test strip is assigned a numerical rating from 0 to 5 using the following scale:

0=no lift observed
1=very slight edge lift
2=up to 25% edge lift
3=26–50% edge lift
4=51–75% edge lift
5=76–100% edge lift Pressure Sensitive Adhesive Residue Test The Pressure Sensitive Adhesive Residue Test is a subjective assessment of the amount of pressure sensitive adhesive left upon the skin after removal of a test strip in accordance with the Skin Adhesion Test. The skin directly underlying each strip is visually inspected to determine the extent to which the area contacted by the pressure sensitive adhesive contains residual pressure sensitive adhesive. Each test strip is assigned a numerical rating from 0 to 5 using the following scale:

0=no visible residue
1=very slight residue
2=residue covering up to 25% of test area
3=residue covering 26–50% of test area
4=residue covering 51–75% of test area
5=residue covering 76–100% of test area Skin Irritation Test The Skin Irritation Test is a subjective assessment of the amount of skin irritation observed after removal of a test strip in accordance with the Skin Adhesion Test. The skin directly underlying each strip is visually inspected. Each test strip is assigned a numerical rating from 0 to 4 using the following scale:

0=no redness or irritation
1=slight redness barely perceptible
2=definite redness
3=definite redness, possible papules, and/or slight raised area (edema)
4=combination of the following: bruising, multiple papules, edema, erythema For each test (skin adhesion, lift, residue and irritation) the value reported for a particular specimen is the average of the values obtained from all of the subjects and all of the test strips of that particular specimen. For example, if there are six subjects and each subject had three strips of the specimen removed at 24 hours, then the $T_{24}$ adhesion value is the average of eighteen independent determinations.

In Vitro Skin Penetration Test Method

The skin penetration data given in the examples below was obtained using the following test method. A diffusion cell is used with either hairless mouse skin or human cadaver skin.

When a transdermal drug delivery device is evaluated, the release liner is removed from a 2.0 $cm^2$ patch and the patch is applied to the skin and pressed to cause uniform contact with the skin. The resulting patch/skin laminate is placed patch side up across the orifice of the lower portion of the diffusion cell. The diffusion cell is assembled and the lower portion is filled with 10 mL of warm (32° C.) receptor fluid so that the receptor fluid is in contact with the skin. The receptor fluid is stirred using a magnetic stirrer. The sampling port is covered except when in use.

The cell is then placed in a constant temperature (32±2° C.) and humidity (50±10% relative humidity) chamber. The receptor fluid is stirred by means of a magnetic stirrer throughout the experiment to assure a uniform sample and a reduced diffusion barrier on the dermal side of the skin. The entire volume of receptor fluid is withdrawn at specified time intervals and immediately replaced with fresh fluid. The withdrawn fluid is filtered through a 0.45 μm filter then analyzed for drug using high performance liquid chromatography. The cumulative percent of drug penetrating the skin and the flux rate are calculated.

Inherent Viscosity Values

The inherent viscosity (IV) values which are reported in the examples below were measured by conventional means using a Cannon-Fenske #50 viscometer in a water bath controlled at 27° C. to measure the flow time of 10 milliliters of a polymer solution (0.15 g per deciliter of polymer in ethyl acetate unless otherwise indicated). The test procedure followed and the apparatus used are described in detail in "Textbook of Polymer Science", F. W. Billmeyer, Wiley Interscience, Second Edition, 1971, pages 84 and 85.

Launderability

Method for Pressing Pressure Sensitive Adhesives onto a Surgical Drape

Laminated pressure sensitive adhesive samples with the release liner removed were pressed onto surgical drapes using weights to mimic the pressure of an arm or an elbow on the drape during surgery. Squares or rectangles that exceeded 7.62 centimeters (cm) in both width and length were cut from the pressure sensitive adhesive samples. The size was larger than the bottom of a silver 8.82 kilogram (kg) weight. The pressure sensitive adhesive sample was applied to a COMPEL™ drape (commercially available from Standard Textile Co., Cincinnati, Ohio) so that there were no wrinkles. The drape with pressure sensitive adhesive sample applied was placed in an oven preheated to 37° C. over a preheated large metal slab and the preheated silver 8.82 kg weight was placed over the pressure sensitive adhesive side of the drape sample. Additional preheated weights (one 2.20 kg, one 11.02 kg, and one 8.82 kg) were placed on top of the initial 8.82 kg weight for a total of 30.87 kg which created a pressure of $13.79 \times 10^3$ Pa pressing the pressure sensitive adhesive sample onto the drape. This assembly was heated for 5 minutes. Then the weight was removed and each pressure sensitive adhesive sample attached to a surgical drape that was ready to be laundered.

Laundering Procedure

The pressure sensitive adhesive samples attached to their respective surgical drapes were laundered in a 143.325 kg (65 pound) load in a commercial washing machine (Milnor 35 washer, Model No. 36021BWE/AEA; Pillerin Milnor Corp., Kenner, La.). The samples went through a typical laundry cycle for surgical linens including: (a) two two-minute alkaline flushes, one cold and one split between hot and cold, in SOLAR BRITE™ Commercial Liquid Laundry Alkali (Ecolab Inc., St. Paul, Minn.); a two-minute hot water flush, an eight-minute hot detergent/suds wash using SOLAR BRITE™ Commercial Liquid Laundry Alkali and DETERGENT 1™ Commercial Liquid Laundry Detergent (Ecolab Inc.); a two-minute hot water flush, an eight-minute hot bleach using OXY BRITE™ Bleach (Ecolab Inc.); three two-minute water rinses, one hot and two split between hot and cold; a four-minute cold sour/soft rinse using SOUR VII™ Acid Sour (Ecolab Inc.) and SO-FRESH™ Freshener (Ecolab Inc.), and a six minute extraction to remove excess liquid.

The pressure sensitive adhesive samples and surgical drapes were dried in a Haubsch dryer at 71° C. for 15 minutes and cooled for 5 minutes.

Each pressure sensitive adhesive sample was inspected for pressure sensitive adhesive release meaning that no pressure sensitive adhesive residue remained on the surgical drape using a scale from 1 (completely detached) to 5 (completely attached). Any rating higher than 1 is a failure while 1 is a pass. Pressure sensitive adhesive samples were also inspected for pressure sensitive adhesive color visibility meaning the iodine was or was not released in the laundry process using a scale from 1 (yellow color) to 3 (colorless). Additionally the pressure sensitive adhesive samples were inspected to determine the amount of pressure sensitive adhesive residue on the drape using a scale of 1 (no residue, easy to peel), 2 (sticky, with residue, but peelable), 3 (unpeelable).

Time to Complete Kill

Direct Inoculation Assay (Qualitative)

Laminated pressure sensitive adhesive samples were cut using a 5 cm$^2$ circular die. The paper release liner was removed. Sterilized TRANSPORE™ Clear First Aid Tape (commercially available from 3M Company, St. Paul, Minn.) was placed aseptically over the polyether polyester backing to provide a stiffer backing to the pressure sensitive adhesive samples. The samples were placed in the bottom of a labeled six-well tissue culture plate with the pressure sensitive adhesive side up. The samples were inoculated with 50 µL of a suspension of *Enterococcus faecalis* (commercially available as "ATCC 10741" from American Type Culture Collection, Rockville, Md.) at a population of approximately 9.0×10$^8$ cfu/mL by spotting 3–4 µL droplets uniformly across the surface of the pressure sensitive adhesive. Inoculated samples were incubated at 37° C. in a humidified incubator until a predetermined time point of 0.5, 1, 2, and 3-hour intervals was reached. Once the time point was reached, the sample was pulled from the incubator and 2 mL of Brain Heart Infusion broth (commercially available from Becton Dickinson and Company, Sparks, Md.) with 0.1% sodium thiosulfate was added to each sample well. The 0.1% sodium thiosulfate neutralized the iodine activity. Once the broth was added to each well, the plate was placed back in the incubator overnight. The following day the optical density of mixed aliquots from under the drape samples in each well of the plates were measured to determine an endpoint of growth or no growth. Time to complete kill (no growth) was recorded.

Preparation of "Dried" Copolymer

In the examples below some of the coating formulations are prepared using "dried" copolymer. Dried copolymer is prepared by knife coating a solution of the copolymer onto a release liner. The copolymer coated release liner is oven dried at an elevated temperature (120–150° C.) to remove solvent and reduce the level of residual monomers. The dried copolymer is then stripped off the release liner and stored in a container.

Preparation of Pyrrolidonoethyl Acrylate (PyEA)

The PyEA used in the examples below was prepared according to the following general method. A 1 liter three-neck round bottom flask is equipped with a paddle stirrer, thermometer with temperature controller, Dean Stark trap with a water cooled condenser and electric heating mantle. To this flask was added N-(hydroxyethyl)pyrrolidin-2-one (260 g, 2 moles), acrylic acid (290 g, 4 moles), toluene (300 mL), p-toluenesulfonic acid hydrate (26 g, 0.14 mole), 4-methoxyphenol (2 g) and copper powder (1 g). Stirring was started and heat applied to the flask contents so that toluene refluxed into the condenser. During the course of the esterification reaction (4.5 hours) approximately 122 mL of water was collected in the trap. The reaction vessel contents were concentrated on a rotoevaporator to provide crude product as a brown liquid. This liquid was distilled under vacuum through a 6 inch (15.2 cm) Vigreux column/water cooled condenser. The first fraction of distillate (acrylic acid) was discarded, after which the PyEA was collected at a boiling point of 115–120° C. at a pressure of 0.2 mm mercury. 260 g of PyEA as a water white liquid was obtained. Analysis by nuclear magnetic resonance spectroscopy showed that this material was 95% pure. The purity level of each lot of PyEA and the desired weight ratio of PyEA are used to determine the amount of PyEA used in the synthesis of a particular copolymer.

Example 1

Isooctyl Acrylate/Pyrrolidonoethyl Acrylate (60/40; IV=0.505)

Isooctyl acrylate (180 g), pyrrolidonoethyl acrylate (120 g), 2,2'-azobis(2,4-dimethylvaleronitrile) (0.6 g), ethyl acetate (291 g), and isopropyl alcohol (9 g) were added to a one liter glass bottle. The bottle was deoxygenated by purging with nitrogen at a one liter per minute flow rate for 2 minutes. The bottle was sealed and placed in a rotating water bath at 45° C. for 24 hours. The percent solids was measured at 47.9%. The inherent viscosity was 0.505 dL/g. A portion of the copolymer was coated at a wet thickness of 9 mil (229 µm) onto a film. The film was oven dried. The compliance of the pressure sensitive adhesive coating was measured using the test method described above and found to be 3.0×10$^{-5}$ cm$^2$/dyne.

Example 2

Isooctyl Acrylate/Pyrrolidonoethyl Acrylate/Methyl Acrylate (40/40/20; IV=0.496)

Isooctyl acrylate (120 g), pyrrolidonoethyl acrylate (120 g), methyl acrylate (60 g), 2,2'-azobis(2,4-dimethylvaleronitrile) (0.6 g), ethyl acetate (263 g), and isopropyl alcohol (13.8 g) were added to a one liter glass bottle. The bottle was deoxygenated by purging with nitrogen at a one liter per minute flow rate for 2 minutes. The bottle was sealed and placed in a rotating water bath at 45° C. for 24 hours. The percent solids was measured at 50.3%. The inherent viscosity was 0.496 dL/g. A portion of the copolymer was coated at a wet thickness of 9 mil (229 µm) onto a film. The film was oven dried. The compliance of the pressure sensitive adhesive coating was measured using the test method described above and found to be 0.8×10$^{-5}$ cm$^2$/dyne.

Example 3

Isooctyl Acrylate/Pyrrolidonoethyl Acrylate/ Polymethyl Methacrylate Macromonomer (54/36/10; IV=0.45)

Isooctyl acrylate (162 g), pyrrolidonoethyl acrylate (108 g), polymethyl methacrylate macromonomer (30 g), 2,2'-azobis(2,4-dimethylvaleronitrile) (0.6 g), ethyl acetate (291 g), and isopropyl alcohol (9 g) were added to a one liter glass bottle. The bottle was deoxygenated by purging with nitrogen at a one liter per minute flow rate for 2 minutes. The bottle was sealed and placed in a rotating water bath at 45° C. for 24 hours. The percent solids was measured at 48.2%. The inherent viscosity was 0.45 dL/g.

Example 4

Isooctyl Acrylate/Pyrrolidonoethyl Acrylate/2-Polystyrylethyl Methacrylate Macromonomer (58.8/39.2/2; IV=0.99)

Isooctyl acrylate (176.6 g), pyrrolidonoethyl acrylate (117.6 g), 2-polystyrylethyl methacrylate macromonomer in cyclohexane at 50% solids (12 g, prepared according to the method of U.S. Pat. No. 5,057,366 Monomer C-2), 2,2'-azobis(2,4-dimethylvaleronitrile) (0.6 g), and ethyl acetate (300 g) were added to a one liter glass bottle. The bottle was deoxygenated by purging with nitrogen at a one liter per minute flow rate for 2 minutes. The bottle was sealed and placed in a rotating water bath at 45° C. for 24 hours. The bottle was removed, opened and 0.6 g of 2,2'-azobis(2,4-dimethylvaleronitrile) in 25 g of ethyl acetate was added. The bottle was deoxygenated as above, sealed and placed in a rotating water bath at 45° C. for 24 hours. The polymer solution was diluted with ethyl acetate (125 g) and mixed until uniform. The percent solids was measured at 36.5%. The inherent viscosity was 0.99 dL/g. A portion of the copolymer was coated onto a 2 mil (51 µm) polyethylene film. The film was oven dried at 110° F. (43° C.) for 20 minutes. The compliance of the pressure sensitive adhesive coating was measured using the test method described above and found to be $1.4 \times 10^{-5}$ cm$^2$/dyne.

Example 5

Isooctyl Acrylate/Pyrrolidonoethyl Acrylate/ Polymethyl Methacrylate Macromonomer (56/37/7; IV=1.02)

Polymethyl methacrylate macromonomer (14 g) and ethyl acetate (200 g) were placed in a one liter amber glass bottle and mixed until the macromonomer was dissolved. Isooctyl acrylate (112 g), 2,2'-azobis(2-methylbutyronitrile) (0.40 g), and pyrrolidonoethyl acrylate (74 g) were added. The bottle was deoxygenated by purging with nitrogen at a one liter per minute flow rate for 2 minutes. The bottle was sealed and placed in a rotating water bath at 57° C. for 24 hours. The polymer solution was diluted to approximately 42 percent solids with ethyl acetate (76.2 g) and mixed overnight. The inherent viscosity was 1.02 dL/g.

Example 6

Isooctyl Acrylate/Pyrrolidonoethyl Acrylate/ Polymethyl Methacrylate Macromonomer (57/38/5; I=0.61)

Polymethyl methacrylate macromonomer (12.5 g), ethyl acetate (302.27 g), and methanol (15.91 g) were placed in a one liter amber glass bottle and mixed until the macromonomer was dissolved. Isooctyl acrylate (142.5 g), 2,2'-azobis(2-methylbutyronitrile) (0.50 g), and pyrrolidonoethyl acrylate (95.0 g) were added. The bottle was deoxygenated by purging with nitrogen at a one liter per minute flow rate for 2 minutes. The bottle was sealed and placed in a rotating water bath at 57° C. for 23 hours. The polymer solution was diluted to approximately 38 percent solids with ethyl acetate (85.20 g) and methanol (4.48 g) and then mixed overnight. The inherent viscosity was 0.61 dL/g.

Example 7

Isooctyl Acrylate/Pyrrolidonoethyl Acrylate/ Polymethyl Methacrylate Macromonomer (57/38/5; IV=0.68*)

Isooctyl acrylate (142.5 g), pyrrolidonoethyl acrylate (95 g), polymethyl methacrylate macromonomer (12.5 g), 2,2'-azobis(2,4-dimethylvaleronitrile) (0.5 g of V-65), and ethyl acetate (375 g) were added to a one liter amber glass bottle. The bottle was deoxygenated by purging with nitrogen at a one liter per minute flow rate for 2 minutes. The bottle was sealed and placed in a rotating water bath at 45° C. for 24 hours. The bottle was removed, opened and 0.5 g of 2,2'-azobis(2,4-dimethylvaleronitrile) was added. The bottle was deoxygenated as above, sealed and placed in a rotating water bath at 45° C. for 24 hours. The inherent viscosity was 0.68 dL/g measured in ethyl acetate at 0.30 g/dL.

Example 8

Isooctyl Acrylate/Pyrrolidonoethyl Acrylate/ Polymethyl Methacrylate Macromonomer (57/38/5; IV=0.85)

Polymethyl methacrylate macromonomer (10 g), ethyl acetate (183.7 g), and isopropyl alcohol (0.9 g) were placed in a one liter amber glass bottle and mixed until the macromonomer was dissolved. Isooctyl acrylate (114 g), 2,2'-azobis(2-methylbutyronitrile) (0.40), and pyrrolidonoethyl acrylate (76 g) were added. The bottle was deoxygenated by purging with nitrogen at a one liter per minute flow rate for 2 minutes. The bottle was sealed and placed in a rotating water bath at 57° C. for 40 hours. The polymer solution was diluted to approximately 42 percent solids with ethyl acetate (91.13 g) and methanol (0.45 g) and then mixed overnight. The inherent viscosity was 0.85 dL/g.

Example 9

Isooctyl Acrylate/Pyrrolidonoethyl Acrylate/ Polymethyl Methacrylate Macromonomer (57/38/5; IV=1.05)

Polymethyl methacrylate macromonomer (12.5 g), ethyl acetate (226.2 g), and methanol (4.2 g) were placed in a one liter amber glass bottle and mixed until the macromonomer was dissolved. Isooctyl acrylate (142.5 g), 2,2'-azobis(2-methylbutyronitrile) (0.50 g), and pyrrolidonoethyl acrylate (95 g) were added. The bottle was deoxygenated by purging with nitrogen at a one liter per minute flow rate for 2 minutes. The bottle was sealed and placed in a rotating water bath at 57° C. for 24 hours. The polymer solution was diluted to approximately 38 percent solids with ethyl acetate (173.55 g) and methanol (3.47 g) and then mixed until uniform. The inherent viscosity was 1.05 dL/g.

Example 10

Isooctyl Acrylate/Pyrrolidonoethyl Acrylate/ Polymethyl Methacrylate Macromonomer (57/38/5; IV=1.13)

Ethyl acetate (325 g), polymethyl methacrylate macromonomer (15 g) and 2,2'-azobis(2,4-dimethylvaleronitrile) (0.60 g) were placed in a one liter amber glass bottle and mixed until all the material was dissolved. Isooctyl acrylate (171 g) and pyrrolidonoethyl acrylate (114 g) were added. The bottle was deoxygenated by purging with nitrogen at a one liter per minute flow rate for 2 minutes. The bottle was sealed and placed in a rotating water bath at 45° C. for 24 hours. The bottle was removed, opened and 0.6 g of 2,2'-azobis(2,4-dimethylvaleronitrile) was added. The bottle was deoxygenated as above, sealed and placed in a rotating water bath at 45° C. for 23 hours. The polymer solution was diluted to about 38 percent solids with ethyl acetate (164.5 g). The inherent viscosity was 1.13 dL/g.

Example 11

Isooctyl Acrylate/Pyrrolidonoethyl Acrylate/ Polymethyl Methacrylate Macromonomer (57/38/5; IV=1.24)

Polymethyl methacrylate macromonomer (12.5 g), ethyl acetate (208.7 g), and methanol (4.3 g) were placed in a one liter amber glass bottle and mixed until the macromonomer was dissolved. Isooctyl acrylate (142.5 g), 2,2'-azobis(2-methylbutyronitrile) (0.50 g), and pyrrolidonoethyl acrylate (95 g) were added. The bottle was deoxygenated by purging with nitrogen at a one liter per minute flow rate for 2 minutes. The bottle was sealed and placed in a rotating water bath at 57° C. for 24 hours. The polymer solution was diluted to approximately 38 percent solids with ethyl acetate (190.99 g) and methanol (3.90 g) and then mixed until uniform. The inherent viscosity was 1.24 dL/g.

Example 12

Isooctyl Acrylate/Pyrrolidonoethyl Acrylate/ Polymethyl Methacrylate Macromonomer (58/39/3; IV=0.50)

Polymethyl methacrylate macromonomer (6 g), ethyl acetate (294 g), and isopropyl alcohol (6 g) were placed in a one liter amber glass bottle and mixed until the macromonomer was dissolved. Isooctyl acrylate (116 g), 2,2'-azobis(2-methylbutyronitrile) (0.40 g), and pyrrolidonoethyl acrylate (84.8 g) were added. The bottle was deoxygenated by purging with nitrogen at a one liter per minute flow rate for 2 minutes. The bottle was sealed and placed in a rotating water bath at 57° C. for 24 hours. The inherent viscosity was 0.50 dL/g.

Example 13

Isooctyl Acrylate/Pyrrolidonoethyl Acrylate/ Polymethyl Methacrylate Macromonomer (58/39/3; IV=0.81)

Polymethyl methacrylate macromonomer (6 g), ethyl acetate (198 g), and isopropyl alcohol (2 g) were placed in a one liter amber glass bottle and mixed until the macromonomer was dissolved. Isooctyl acrylate (116 g), 2,2'-azobis(2-methylbutyronitrile) (0.40 g), and pyrrolidonoethyl acrylate (78 g) were added. The bottle was deoxygenated by purging with nitrogen at a one liter per minute flow rate for 2 rminutes. The bottle was sealed and placed in a rotating water bath at 57° C. for 24 hours. The polymer solution was diluted to approximately 42 percent solids with ethyl acetate (75.4 g) and isopropyl alcohol (0.76 g) and then mixed until uniform. The inherent viscosity was 0.81 dL/g.

Example 14

Isooctyl Acrylate/Pyrrolidonoethyl Acrylate/ Polymethyl Methacrylate Macromonomer (58/39/3; IV=1.02)

Ethyl acetate (198 g), isopropyl alcohol (2.0 g) and polymethyl methacrylate macromonomer (6 g) were placed in a one liter amber glass bottle and mixed until the macromonomer was dissolved. Isooctyl acrylate (116 g), 2,2'-azobis(2-methylbutyronitrile) (0.40 g), and pyrrolidonoethyl acrylate (78 g) were added. The bottle was deoxygenated by purging with nitrogen at a one liter per minute flow rate for 2 minutes. The bottle was sealed and placed in a rotating water bath at 57° C. for 24 hours. The polymer solution was diluted to approximately 40 percent solids with ethyl acetate (99 g) and isopropyl alcohol (1 g) and then mixed until uniform. The inherent viscosity was 1.02 dL/g.

Example 15

Isooctyl Acrylate/Pyrrolidonoethyl Acrylate/ Polymethyl Methacrylate Macromonomer (58/39/3; V=1.08)

Polymethyl methacrylate macromonomer (6 g) and ethyl acetate (234.8 g) were placed in a one liter amber glass bottle and mixed until the macromonomer was dissolved. Isooctyl acrylate (116 g), 2,2'-azobis(2-methylbutyronitrile) (0.40 g), and pyrrolidonoethyl acrylate (78 g) were added. The bottle was deoxygenated by purging with nitrogen at a one liter per minute flow rate for 2 minutes. The bottle was sealed and placed in a rotating water bath at 57° C. for 24 hours. The polymer solution was diluted to approximately 42 percent solids with ethyl acetate (41.4 g) and then mixed until uniform. The inherent viscosity was 1.08 dL/g.

Example 16

Isooctyl Acrylate/Pyrrolidonoethyl Acrylate/ Polymethyl Methacrylate Macromonomer (59/39/2; I=0.95)

Ethyl acetate (174.0 g), isopropyl alcohol (3.6 g) and polymethyl methacrylate macromonomer (4 g) were placed in a one liter amber glass bottle and mixed until the macromonomer was dissolved. Isooctyl acrylate (118 g), 2,2'-azobis(2-methylbutyronitrile) (0.4 g), and pyrrolidonoethyl acrylate (80.8 g) were added. The bottle was deoxygenated by purging with nitrogen at a one liter per minute flow rate for 2 minutes. The bottle was sealed and placed in a rotating water bath at 57° C. for 24 hours. The polymer solution was diluted to about 40 percent solids with ethyl acetate (119.95 g) and isopropyl alcohol (2.45 g) and then mixed until uniform. The inherent viscosity was 0.95 dL/g.

Example 17

Isooctyl Acrylate/Pyrrolidonoethyl Acrylate/ Polymethyl Methacrylate Macromonomer (59/39/2; IV=1.12)

Ethyl acetate (352.8 g), isopropyl alcohol (7.2 g) and polymethyl methacrylate macromonomer (4.8 g) were placed in a one liter amber glass bottle and mixed until the macromonomer was dissolved. Isooctyl acrylate (141.6 g), 2,2'-azobis(2-methylbutyronitrile) (0.48 g), and pyrrolidonoethyl acrylate (93.6 g) were added. The bottle was deoxygenated by purging with nitrogen at a one liter per minute flow rate for 2 minutes. The bottle was sealed and placed in a rotating water bath at 57° C. for 24 hours. The inherent viscosity was 1.12 dL/g.

Example 18

Isooctyl Acrylate/Pyrrolidonoethyl Acrylate/ Polymethyl Methacrylate Macromonomer (59/39/2; IV=1.24)

Ethyl acetate (198 g), isopropyl alcohol (2 g) and polymethyl methacrylate macromonomer (4 g) were placed in a one liter amber glass bottle and mixed until the macromonomer was dissolved. Isooctyl acrylate (118 g), 2,2'-azobis(2-methylbutyronitrile) (0.4 g), and pyrrolidonoethyl acrylate (83.4 g) were added. The bottle was deoxygenated by purging with nitrogen at a one liter per minute flow rate for 2 minutes. The bottle was sealed and placed in a rotating water bath at 57° C. for 25 hours. The polymer solution was diluted to about 40 percent solids with ethyl acetate (169.7 g) and isopropyl alcohol (1.71g) and then mixed until uniform. The inherent viscosity was 1.24 dL/g.

Example 19

Isooctyl Acrylate/Pyrrolidonoethyl Acrylate/Polymethyl Methacrylate Macromonomer (67/28/5; IV=1.38)

Ethyl acetate (325 g) and polymethyl methacrylate macromonomer (15 g) were placed in a one liter amber glass bottle and mixed until the macromonomer was dissolved. Isooctyl acrylate (201 g), 2,2'-azobis(2,4-dimethylvaleronitrile) (0.60 g), and pyrrolidonoethyl acrylate (84 g) were added. The bottle was deoxygenated by purging with nitrogen at a one liter per minute flow rate for 2 minutes. The bottle was sealed and placed in a rotating water bath at 45° C. for 20 hours. The bottle was removed, opened and 0.6 g of 2,2'-azobis(2,4-dimethylvaleronitrile) was added. The bottle was deoxygenated as above, sealed and placed in a rotating water bath at 45° C. for 28 hours. The polymer solution was diluted with ethyl acetate (164.5 g) then mixed until uniform. The inherent viscosity was 1.38 dL/g.

Example 20

Isooctyl Acrylate/Pyrrolidonoethyl Acrylate/Polymethyl Methacrylate Macromonomer (77/18/5; IV=1.13)

Ethyl acetate (325 g) and polymethyl methacrylate macromonomer (15 g) were placed in a one liter amber glass bottle and mixed until the macromonomer was dissolved. Isooctyl acrylate (231 g), 2,2'-azobis(2,4-dimethylvaleronitrile) (0.60 g), and pyrrolidonoethyl acrylate (54 g) were added. The bottle was deoxygenated by purging with nitrogen at a one liter per minute flow rate for 2 minutes. The bottle was sealed and placed in a rotating water bath at 45° C. for 20 hours. The bottle was removed, opened and 0.6 g of 2,2'-azobis(2,4-dimethylvaleronitrile) was added. The bottle was deoxygenated as above, sealed and placed in a rotating water bath at 45° C. for 28 hours. The polymer solution was diluted with ethyl acetate (164.5 g) then mixed until uniform. The inherent viscosity was 1.13 dL/g.

Example 21

Isooctyl Acrylate/Pyrrolidonoethyl Acrylate/Polymethyl Methacrylate Macromonomer (67/28/5; V=0.52)

Ethyl acetate (255 g) and polymethyl methacrylate macromonomer (7.5g) were placed in a glass bottle and mixed until all of the macromonomer had dissolved. Isooctyl acrylate (100.5 g), pyrrolidonoethyl acrylate (42 g) and 2,2'-azobis(2-methylbutyronitrile) (0.4 g) were added. The bottle was deoxygenated by purging with nitrogen for 2 minutes. The bottle was sealed and placed in a rotating water bath at 57° C. for 24 hours. The bottle was removed, opened and 0.3 g of 2,2'-azobis(2-methylbutyronitrile) was added. The bottle was deoxygenated as above, sealed and placed in a rotating water bath at 57° C. for 24 hours. The inherent viscosity was 0.52 dL/g.

Example 22

Isooctyl Acrylate/Pyrrolidonoethyl Acrylate/Vinyl Acetate/Polymethyl Methacrylate Macromonomer (62/15/20/3; IV=1.16)

Polymethyl methacrylate macromonomer (5.25 g), ethyl acetate (232.0 g) and methanol (9.67 g) were placed in a one liter amber glass bottle and mixed until all of the macromonomer had dissolved. Isooctyl acrylate (108.25 g), pyrrolidonoethyl acrylate (27.9 g), vinyl acetate (35 g) and 2,2'-azobis(2-methylbutyronitrile) (0.35 g) were added. The bottle was deoxygenated by purging with nitrogen for 2 minutes. The bottle was sealed and placed in a rotating water bath at 57° C. for 24 hrs. The polymer solution was diluted with ethyl acetate (200.0 g) and methanol (8.33 g) and mixed until homogeneous. The inherent viscosity was 1.16 dL/g.

Example 23

Isooctyl Acrylate/Pyrrolidonoethyl Acrylate/Vinyl Acetate/Polymethyl Methacrylate Macromonomer (62/15/20/3; IV=1.00)

Polymethyl methacrylate macromonomer (5.25 g), vinyl acetate (35 g), ethyl acetate (232 g) and methanol (9.67 g) were placed in a one liter amber glass bottle and mixed until all of the macromonomer had dissolved. Isooctyl acrylate (108.25 g), pyrrolidonoethyl acrylate (27.9 g), and 2,2'-azobis(2-methylbutyronitrile) (0.35 g) were added. The bottle was deoxygenated by purging with nitrogen for 2 minutes. The bottle was sealed and placed in a rotating water bath at 57° C. for 24 hrs. The polymer solution was diluted with ethyl acetate (122.3 g) and mixed until homogeneous. The inherent viscosity was 1.00 dL/g.

Example 24

Isooctyl Acrylate/Pyrrolidonoethyl Acrylate/Vinyl Acetate/Polymethyl Methacrylate Macromonomer (63/15/20/2; IV=1.21)

Polymethyl methacrylate macromonomer (3.5 g), vinyl acetate (35 g), ethyl acetate (232 g) and methanol (9.67 g) were placed in a one liter amber glass bottle and mixed until all of the macromonomer had dissolved. Isooctyl acrylate (110.25 g), pyrrolidonoethyl acrylate (27.9 g), and 2,2'-azobis(2-methylbutyronitrile) (0.35 g) were added. The bottle was deoxygenated by purging with nitrogen for 2 minutes. The bottle was sealed and placed in a rotating water bath at 57° C. for 24 hrs. The polymer solution was diluted with ethyl acetate (127.97 g) and mixed until homogeneous. The inherent viscosity was 1.21 dL/g.

Example 25

Isooctyl Acrylate/Pyrrolidonoethyl Acrylate/Vinyl Acetate/Polymethyl Methacrylate Macromonomer (62/15/20/3; IV=1.46)

Polymethyl methacrylate macromonomer (5.25 g), ethyl acetate (220.5 g) and methanol (2.23 g) were placed in a one liter amber glass bottle and mixed until all of the macromonomer had dissolved. Isooctyl acrylate (108.25 g), pyrrolidonoethyl acrylate (27.9 g), vinyl acetate (35 g) and 2,2'-azobis(2-methylbutyronitrile) (0.35 g) were added. The bottle was deoxygenated by purging with nitrogen for 2 minutes. The bottle was sealed and placed in a rotating water bath at 57° C. for 24 hrs. The polymer solution was diluted with ethyl acetate (224.99 g) and methanol (2.27 g) and mixed until homogeneous. The inherent viscosity was 1.46 dL/g.

Example 26

Isooctyl Acrylate/Pyrrolidonoethyl Acrylate/Vinyl Acetate/Polymethyl Methacrylate Macromonomer (63/15/20/2; IV=1.47)

Polymethyl methacrylate macromonomer (3.5 g), ethyl acetate (201.33 g) and methanol (4.12 g) were placed in a one liter amber glass bottle and mixed until all of the macromonomer had dissolved. Isooctyl acrylate (110.25 g), pyrrolidonoethyl acrylate (27.9 g), vinyl acetate (35 g) and 2,2'-azobis(2-methylbutyronitrile) (0.35 g) were added. The bottle was deoxygenated by purging with nitrogen for 2 minutes. The bottle was sealed and placed in a rotating water bath at 57° C. for 24 hrs. The polymer solution was diluted to approximately 28 percent solids with ethyl acetate (239.76 g) and methanol (4.90 g) and mixed until homogeneous. The inherent viscosity was 1.47 dL/g.

Example 27

Isooctyl Acrylate/Pyrrolidonoethyl Acrylate/Acrylic Acid/4-Acryloyloxybenzophenone 80/15/5/0.1

Isooctyl acrylate (19.2 g), pyrrolidonoethyl acrylate (3.6 g), acrylic acid (1.2 g), 4-acryloyloxybenzophenone (0.11 g), 2,2'azobis(isobutyronitrile) (0.072 g ), and ethyl acetate (36 g) were combined. The polymerization was run at 55° C. for 24 hours. The resulting polymer solution was diluted to 30 percent solids with ethyl acetate (19 g) and isopropyl alcohol (1 g). The polymer solution was coated onto a silicone release liner and dried at 65° C. for 15 minutes. The dried pressure sensitive adhesive coating had a thickness of 50 µm. The dried coating was UV crosslinked (using a Fusion H-bulb) with a total dose of 140 mJ/cm².

Example 28

Isooctyl Acrylate/Pyrrolidonoethyl Acrylate/Acrylic Acid/4-Acryloyloxybenzophenone 80/18/2/0.1

Isooctyl acrylate (19.2 g), pyrrolidonoethyl acrylate (4.32 g), acrylic acid (0.48 g), 4-acryloyloxybenzophenone (0.11 g), 2,2'azobis(isobutyronitrile) (0.072 g), and ethyl acetate (36 g) were combined. The polymerization was run at 55° C. for 24 hours. The resulting polymer solution was diluted to 30 percent solids with ethyl acetate (19 g) and isopropyl alcohol (1 g). The polymer solution was coated onto a silicone release liner and dried at 65° C. for 15 minutes. The dried pressure sensitive adhesive coating had a thickness of 50 µm. The dried coating was UV crosslinked (using a Fusion H-bulb) with a total dose of 140 mJ/cm².

The pressure sensitive adhesives of Examples 27 and 28 were used to bond two layers of polyvinyl chloride and the strength of the resulting pressure sensitive adhesive bond was measured as follows. A strip of the pressure sensitive adhesive coated liner having a width of 0.5 inches (1.27 cm) was placed pressure sensitive adhesive side down on a strip of PANAFLEX™ 945 substrate (available from 3M Company, St. Paul, Minn.) having a width of 1 inch (2.54 cm). The pressure sensitive adhesive was rolled down from the liner to the substrate using 6 passes with a 2.0 kg rubber covered hand roller. The liner was removed; a strip of PANAFLEX™ 945 was placed on the exposed pressure sensitive adhesive and then rolled down using 6 passes with a 2.0 kg rubber covered hand roller.

T-peel adhesion was determined as follows. The first inch of the laminate was separated into two layers. The free end of the first layer was clamped into the lower jar of a tensile tester. The free end of the second layer was clamped into the upper jaw of the tensile tester. The two layers were peeled away from each other at a rate of 12 inches/minute (30 cm/minute).

T-peel adhesion was measured on samples immediately after they were prepared (initial adhesion), after they had been conditioned for 24 hours in a constant temperature (23±2° C.) and humidity (50±5 percent relative humidity) room (CTH), and after they had been aged in an oven at 158° F. (70° C.) for 1 week followed by 2 days in a constant temperature (23±2° C.) and humidity (50±5 percent relative humidity) room. The results are shown in Table 1 below.

TABLE 1

|  | T-peel Adhesion (g/cm) | |
| --- | --- | --- |
| Conditions | Example 27 | Example 28 |
| Initial | 326 | 301 |
| 24 hrs CTH | 431 | 325 |
| 1 wk at 70° C. + 2 days CTH | 602 | 355 |

Examples 29–40

A series of pressure sensitive adhesive coated sheet materials having a coating containing 25% ethyl oleate were prepared using the copolymers of Examples 5, 6, 8, 9, and 11–18. The following general procedure was used. The wet copolymer was coated onto a release liner at a 10 mil (254 µm) wet thickness and then oven dried at 250° F. (121° C.) for 20 minutes. The dried copolymer was stripped from the release liner and stored in a glass jar for later use. Dried copolymer (60 g), ethyl oleate (20 g), and ethyl acetate (75 g) were combined in a glass jar. The jar was sealed and put on a roller mixer overnight. The resulting formulation was coated onto a release liner at a wet thickness of 16–21 mil (406–533 µm). The coated release liner was air dried at ambient conditions for 5 minutes, then oven dried at 110° F. (43° C.) for 4 minutes, at 185° F. (85° C.) for 2 minutes, and at 225° F. (107° C.) for 2 minutes. After cooling to ambient temperature the coated liner was laminated to a two-side corona treated 3 mil (76 µm) polyethylene backing. The laminate was stored in a sealed pouch until used for testing. The compliance, tack, adhesion to VITRO-SKIN™ substrate, and adhesion to stainless steel were measured using the test methods described above. The results are shown in Table 2 below which also shows the copolymer used and the coating thickness after drying. These materials were also tested in skin panels using the methods described above. The results are shown in Table 3 below where "fall-off" indicates the number of strips that had fallen off the skin prior to measuring the adhesion at that time point.

TABLE 2

IOA/PyEA/PMMAMac Copolymers Formulated with 25% Ethyl Oleate

| Example Number | Copolymer | IV (dL/g) | Thickness (mil/μm) | Compliance × $10^{-5}$ cm$^2$/dyne | Tack (g) | Adhesion (g/cm) Vitro-Skin | Adhesion (g/cm) Steel |
|---|---|---|---|---|---|---|---|
| 29 | IOA/PyEA/PMMAMac 56/37/7 | 1.02 | 4.5/114 | 4.1 ± 0.7 | 127 | 9 | 15 |
| 30 | IOA/PyEA/PMMAMac 57/38/5 | 1.24 | 4.5/114 | 5.0 ± 1.0 | 154 | 15 | 27 |
| 31 | IOA/PyEA/PMMAMac 57/38/5 | 1.05 | 4.5/114 | 4.3 ± 0.8 | 196 | 16 | 23 |
| 32 | IOA/PyEA/PMMAMac 57/38/5 | 0.85 | 4.5/114 | 4.8 ± 0.3 | 157 | 15 | 19 |
| 33 | IOA/PyEA/PMMAMac 57/38/5 | 0.61 | 5.0/127 | 6.5 ± 0.6 | 245 | 15 | 31 |
| 34 | IOA/PyEA/PMMAMac 58/39/3 | 1.08 | 5.0/127 | 10.9 ± 1.5 | 172 | 28 | 43 |
| 35 | IOA/PyEA/PMMAMac 58/39/3 | 1.02 | 5.0/127 | 13.6 ± 2.6 | 214 | 24 | 39 |
| 36 | IOA/PyEA/PMMAMac 58/39/3 | 0.81 | 5.0/127 | 14.5 ± 2.1 | 221 | 27 | 45 |
| 37 | IOA/PyEA/PMMAMac 58/39/3 | 0.50 | 5.5140 | 70.1 ± 4.8 | 157 | 43 | 63 |
| 38 | IOA/PyEA/PMMAMac 59/39/2 | 1.24 | 5.3/135 | 14.2 ± 1.2 | 332 | 40 | 54 |
| 39 | IOA/PyEA/PMMAMac 59/39/2 | 1.12 | 4.5/114 | 22.9 ± 0.9 | 215 | 31 | 39 |
| 40 | IOA/PyEA/PMMAMac 59/39/2 | 0.95 | 4.5/114 | 35.8 ± 3.9 | 244 | 46 | — |

TABLE 3

Skin Panel Results
IOA/PyEA/PMMAMac Copolymers Formulated with 25% Ethyl Oleate

| Example Number | Copolymer | IV (dL/g) | Adhesion (g/cm) $T_0$ | Adhesion (g/cm) $T_{24}$ | Adhesion (g/cm) $T_{72}$ | Lift $T_{24}$ | Lift $T_{72}$ | Fall-off $T_{24}$ | Fall-off $T_{72}$ | Residue $T_{24}$ | Residue $T_{72}$ | Irritation $T_{24}$ | Irritation $T_{72}$ |
|---|---|---|---|---|---|---|---|---|---|---|---|---|---|
| 29 | IOA/PyEA/PMMAMac 56/37/7 | 1.02 | 24 | 8 | 6 | 3.3 | 3.8 | 4 | 7 | 0.0 | 0.0 | 0.6 | 0.3 |
| 30 | IOA/PyEA/PMMAMac 57/38/5 | 1.24 | 36 | 16 | 13 | 1.4 | 3.5 | 1 | 6 | 0.0 | 0.0 | 0.5 | 1.1 |
| 31 | IOA/PyEA/PMMAMac 57/38/5 | 1.05 | 37 | 21 | 13 | 1.8 | 3.3 | 0 | 5 | 0.0 | 0.0 | 0.8 | 0.7 |
| 32 | IOA/PyEA/PMMAMac 57/38/5 | 0.85 | 35 | 13 | 9 | 2.5 | 3.1 | 2 | 5 | 0.0 | 0.0 | 0.4 | 0.3 |
| 33 | IOA/PyEA/PMMAMac 57/38/5 | 0.61 | 43 | 26 | 24 | 1.3 | 3.4 | 0 | 3 | 0.0 | 0.3 | 0.3 | 0.8 |
| 34 | IOA/PyEA/PMMAMac 58/39/3 | 1.08 | 61 | 25 | 22 | 0.2 | 2.1 | 0 | 2 | 0.2 | 0.1 | 0.7 | 1.3 |
| 35 | IOA/PyEA/PMMAMac 58/39/3 | 1.02 | 69 | 35 | 34 | 0.8 | 2.3 | 0 | 1 | 0.3 | 0.6 | 0.3 | 1.3 |
| 36 | IOA/PyEA/PMMAMac 58/39/3 | 0.81 | 74 | 39 | 25 | 0.8 | 1.8 | 0 | 2 | 0.4 | 0.4 | 0.3 | 1.3 |
| 37 | IOA/PyEA/PMMAMac 58/39/3 | 0.50 | — | 48 | 35 | 0.8 | 1.3 | 0 | 0 | 3.5 | 3.0 | 1.5 | 1.3 |
| 38 | IOA/PyEA/PMMAMac 59/39/2 | 1.24 | — | 39 | 34 | 1.3 | 1.3 | 2 | 2 | 1.3 | 1.3 | 0.8 | 1.3 |
| 39 | IOA/PyEA/PMMAMac 59/39/2 | 1.12 | 103 | 43 | 38 | 0.1 | 0.5 | 0 | 0 | 0.4 | 1.0 | 0.8 | 1.4 |
| 40 | IOA/PyEA/PMMAMac 59/39/2 | 0.95 | 159 | 49 | 61 | 0.0 | 0.3 | 0 | 0 | 1.0 | 1.8 | 0.8 | 2.1 |

Examples 41–45

A series of pressure sensitive adhesive coated sheet materials having a coating containing 25% ethyl oleate were prepared using the copolymers of Examples 22–26. The general procedure for Examples 29–40 was used. The compliance, tack, adhesion to Vitro-Skin substrate, and adhesion to stainless steel were measured using the test methods described above. The results are shown in Table 4 below which also shows the copolymer used and the coating thickness after drying. These materials were also tested in skin panels using the methods described above. The results are shown in Table 5 below.

TABLE 4

IOA/PyEA/VOAc/PMMAMac Copolymers Formulated with 25% Ethyl Oleate

| Example Number | Copolymer | IV (dL/g) | Thickness (mil/μm) | Compliance × $10^{-5}$ cm$^2$/dyne | Tack (g) | Adhesion (g/cm) Vitro Skin | Adhesion (g/cm) Steel |
|---|---|---|---|---|---|---|---|
| 41 | IOA/PyEA/VOAc/PMMAMac 62/15/20/3 | 1.16 | 4.25/108 | 3.94 ± 0.06 | 308 | 48 | 63 |
| 42 | IOA/PyEA/VOAc/PMMAMac 62/15/20/3 | 1.00 | 6.0/152 | 4.46 ± 0.18 | 322 | 50 | 101 |
| 43 | IOA/PyEA/VOAc/PMMAMac 63/15/20/2 | 1.21 | 5.5/140 | 8.09 ± 0.46 | 283 | 78 | 195 |
| 44 | IOA/PyEA/VOAc/PMMAMac 62/15/20/3 | 1.46 | 4.5/114 | 2.98 ± 0.06 | 294 | 43 | 63 |
| 45 | IOA/PyEA/VOAc/PMMAMac 63/15/20/2 | 1.47 | 5.5/140 | 5.75 ± 0.61 | 316 | 71 | 93 |

TABLE 5

Skin Panel Results
IOA/PyEA/VOAc/PMMAMac Copolymers Formulated with 25% Ethyl Oleate

| Example Number | Copolymer | IV (dL/g) | Adhesion (g/cm) $T_0$ | $T_{24}$ | $T_{72}$ | Lift $T_{24}$ | $T_{72}$ | Fall-off $T_{24}$ | $T_{72}$ | Residue $T_{24}$ | $T_{72}$ | Irritation $T_{24}$ | $T_{72}$ |
|---|---|---|---|---|---|---|---|---|---|---|---|---|---|
| 41 | IOA/PyEA/VOAc/PMMAMac 62/15/20/3 | 1.16 | 63 | 46 | 15 | 1.6 | 3.3 | 0 | 5 | 0.2 | 0.1 | 0.9 | 0.9 |
| 42 | IOA/PyEA/VOAc/PMMAMac 62/15/20/3 | 1.00 | 69 | 36 | 40 | 1.8 | 2.7 | 1 | 1 | 0.3 | 0.2 | 0.3 | 0.8 |
| 43 | IOA/PyEA/VOAc/PMMAMac 63/15/20/2 | 1.21 | 151 | 63 | 76 | 0.2 | 1.1 | 0 | 0 | 1.9 | 1.5 | 0.8 | 1.2 |
| 44 | IOA/PyEA/VOAc/PMMAMac 62/15/20/3 | 1.46 | 50 | 34 | 29 | 1.5 | 2.1 | 0 | 2 | 0.7 | 0.1 | 0.8 | 0.6 |
| 45 | IOA/PyEA/VOAc/PMMAMac 63/15/20/2 | 1.47 | 107 | 57 | 38 | 0.5 | 1.9 | 0 | 2 | 0.7 | 0.6 | 0.4 | 0.6 |

Examples 46–49

Dried copolymer (5.035 g of IOA/PyEA/PMMAMac 67/28/5 IV=1.38, Example 19), atenolol (0.226 g), lauramine oxide (0.128 g), caprylic acid (2.143 g) and solvent (11.038 g of 90/10 ethyl acetate/methanol) were combined and mixed overnight on a platform shaker to provide a homogeneous coating formulation. The formulation was coated at a wet thickness of 15 mil (381 μm) onto a silicone release liner. The coated release liner was oven dried at 110° F. (43° C.) for 5 minutes and then allowed to air dry at ambient conditions for one hour. The resulting pressure sensitive adhesive coating contained 3.0 percent atenolol, 1.7 percent lauramine oxide and 28.5 percent caprylic acid. The coated liner was then laminated to a backing (COTRAN™ polyolefin film from 3M Company).

Using the same copolymer and the same general method additional transdermal drug delivery devices were prepared. The weight percent of atenolol and the identity and weight percent of the excipients used are shown in Table 6 below.

The laminates were die cut into 2 cm² patches. The penetration through hairless mouse skin was determined using the test method described above. The receptor fluid was phosphate buffer. The receptor fluid was removed after 24 hours and analyzed for atenolol using HPLC. The HPLC conditions were as follows: column: Inertsil 5 ODS3, 150× 4.6 mm, 5 μm particle size; mobile phase: 10 mM phosphate buffer/methanol/isopropyl alcohol (85/15/1 v/v/v); flow rate: 1.0 mL/minute; detector: UV, 226 nm at 0.4 AUFS; run time: 10 minutes; injection volume: 20 μL. The flux and percent of drug penetrating are shown in Table 6 below where each value is the average of three independent determinations.

Patches (5.0 cm²) were cut from the laminate of Example 48. The tack was measured using the test method described above and found to be 278 g.

TABLE 6

IOA/PyEA/PMMAMac Copolymer Formulated with Atenolol
In Vitro Hairless Mouse Skin Penetration

| Example Number | Atenolol | Lauramine Oxide | Benzyl Alcohol | Caprylic Acid | Flux (24 hr) μg/cm²/hr | % Drug Penetrating |
|---|---|---|---|---|---|---|
| 46 | 3.0 | 1.7 | 0.0 | 28.5 | 1.8 | 12.1 |
| 47 | 3.1 | 2.3 | 20.7 | 7.3 | 1.7 | 12.2 |
| 48 | 3.1 | 3.0 | 27.0 | 0.0 | 2.4 | 19.1 |
| 49 | 3.1 | 0.0 | 29.6 | 0.0 | 1.8 | 12.5 |

Examples 50–69

Using the general method of Example 46, a series of transdermal drug delivery devices was prepared. In all instances the pressure sensitive adhesive coating contained 3.0 percent by weight of atenolol and the copolymer used was IOA/PyEA/PMMAMac 67/28/5 IV=0.52, Example 21. Table 8 below shows the amount and identity of the excipients. Penetration from 2.0 cm² patches through human cadaver skin was determined using the test method described above. Samples of receptor fluid were taken at 6, 12, and 24 hours. The average 24 hour cumulative flux and the percent drug penetrating are shown in Table 7 below where each value is the average of three independent determinations.

Patches (5.0 cm²) were cut from the laminates of Examples 53, 54 and 56. The tack was measured using the test method described above and found to be 279 g, 62 g and 143 g respectively.

TABLE 7

IOA/PyEA/PMMAMac Copolymer Formulated with Atenolol
In Vitro Human Cadaver Skin Penetration

| Example Number | Benzyl Alcohol | Caprylic Acid | Glyceryl Monolaurate | Lauramine Oxide | Flux $\mu g/cm^2/hr$ | % Drug Penetrating |
|---|---|---|---|---|---|---|
| 50 | 30.0 | 0.0 | 0.0 | 0.0 | 3.2 | 19.1 |
| 51 | 0.0 | 30.0 | 0.0 | 0.0 | 3.7 | 22.8 |
| 52 | 27.7 | 0.0 | 3.2 | 0.0 | 3.0 | 29.9 |
| 53 | 0.0 | 27.0 | 3.0 | 0.0 | 5.7 | 25.1 |
| 54 | 27.0 | 0.0 | 0.0 | 2.9 | 8.1 | 48.5 |
| 55 | 0.0 | 27.0 | 0.0 | 3.0 | 3.4 | 20.4 |
| 56 | 24.4 | 0.0 | 3.1 | 3.0 | 11.8 | 49.4 |
| 57 | 0.0 | 24.0 | 3.0 | 3.0 | 4.0 | 20.7 |
| 58 | 15.2 | 13.9 | 0.0 | 0.0 | 2.2 | 20.7 |
| 59 | 28.5 | 0.0 | 1.5 | 0.0 | 1.2 | 6.1 |
| 60 | 0.0 | 28.5 | 1.5 | 0.0 | 1.4 | 11.2 |
| 61 | 28.6 | 0.0 | 1.5 | 0.0 | 4.7 | 23.0 |
| 62 | 0.0 | 28.4 | 0.0 | 1.6 | 3.6 | 22.9 |
| 63 | 13.5 | 13.6 | 2.9 | 0.0 | 2.7 | 14.3 |
| 64 | 13.8 | 13.7 | 0.0 | 2.9 | 3.1 | 26.0 |
| 65 | 11.9 | 12.0 | 3.0 | 3.0 | 3.3 | 25.8 |
| 66 | 20.9 | 7.5 | 0.8 | 0.7 | 2.4 | 15.4 |
| 67 | 7.5 | 20.9 | 0.8 | 0.8 | 2.6 | 17.4 |
| 68 | 18.0 | 7.4 | 2.2 | 2.2 | 4.4 | 31.8 |
| 69 | 7.5 | 18.2 | 2.2 | 2.2 | 2.8 | 20.8 |

Examples 70–77

Dried copolymer (3.967 g, IOA/PyEA/PMMAMac 67/28/5 IV=1.38, Example 19), methol (1.272 g), propylene glycol (1.2863 g), testosterone (0.2405) and solvent (18.0 g of 90/10 ethyl acetate/methanol) were combined and mixed on a platform shaker until a homogeneous coating formulation was obtained. The formulation was coated at a wet thickness of 22 mil (559 $\mu$m) onto a silicone release liner. The coated release liner was allowed to dry at ambient temperature for 1 minute then it was oven dried at 110° F. (43° C.) for 10 minutes. Assuming that 15 percent of the menthol and 44 percent of the propylene glycol were lost on drying, then the resulting pressure sensitive adhesive coating contained 4 percent testosterone, 18 percent menthol, 12 percent propylene glycol and 66 percent copolymer. (Note: "Loss on drying" factors may be easily determined by one skilled in the art by using conventional drying experiments. That is, coating a formulation containing a known amount of excipient onto a release liner, drying the coated release liner under controlled conditions, determining the amount of excipient in the resulting coating, and calculating the amount lost on drying.) The coated liner was then laminated to a 3 mil (76 $\mu$m) polyethylene backing.

Using the same copolymer and the same general method additional transdermal delivery devices were prepared. Devices were also prepared using a IOA/PyEA/PMMAMac 57/38/5 IV=1.13 copolymer (Example 10) and the same general method except that the wet coating thickness was 23 mils (584 $\mu$m). The weight percent of testosterone and the identity and weight percent of the copolymer and excipients are shown in Table 8 below.

The laminates were die cut into 2 $cm^2$ patches. The penetration through human cadaver skin was determined using the test method described above. The receptor fluid was 30 percent N-methyl-2-pyrrolidone in water. The receptor fluid was removed after 24 hours and analyzed for testosterone using HPLC. The HPLC conditions were as follows: column: Supelcosil LC-18, 150×4.6 mm, 5 $\mu$m particle size; mobile phase: 60 percent deaerated water, 40 percent HPLC grade acetonitrile; flow rate: 2 mL/minute; detector: UV, 241 nm at 0.2 AUFS; run time: 5 minutes; injection volume: 20 $\mu$L. The flux and percent of drug penetrating are shown in Table 8 below where each value is the average of three independent determinations.

Patches (5.0 $cm^2$) were cut from the laminates of Examples 71 and 75. The tack and compliance were measured using the test method described above. The tack values were 190 g and 262 g respectively with each value being the average of four independent determinations. The compliance values were 9.25×10$^{-5}$ $cm^2$/dynes and 6.17×10$^{-5}$ $cm^2$/dynes respectively with each value being the average of four independent determinations. After 5 days it was observed that crystals had formed in the laminates of Examples 72 and 76.

TABLE 8

IOA/PyEA/PMMAMac Copolymers Formulated with Testosterone
In Vitro Human Cadaver Skin Penetration

| Example Number | Copolymer | Testosterone | Menthol | Propylene Glycol | Lauramine Oxide | Flux $\mu g/cm^2/hr$ | % Drug Penetrating |
|---|---|---|---|---|---|---|---|
| 70 | 66.0% 67/28/5 | 4.0% | 18.0% | 12.0% | 0% | 8.10 | 26.7 |
| 71 | 64.0% 67/28/5 | 6.0% | 18.0% | 12.0% | 0% | 8.52 | 18.8 |
| 72 | 62.0% 67/28/5 | 8.0% | 18.0% | 12.0% | 0% | 11.03 | 18.2 |
| 73 | 64.0% 67/28/5 | 4.0% | 18.0% | 12.0% | 2.0% | 10.63 | 44.4 |
| 74 | 66.0% 57/38/5 | 4.0% | 18.0% | 12.0% | 0% | 6.24 | 27.8 |

TABLE 8-continued

IOA/PyEA/PMMAMac Copolymers Formulated with Testosterone
In Vitro Human Cadaver Skin Penetration

| Example Number | Copolymer | Testosterone | Menthol | Propylene Glycol | Lauramine Oxide | Flux µg/cm²/hr | % Drug Penetrating |
|---|---|---|---|---|---|---|---|
| 75 | 64.0% 57/38/5 | 6.0% | 18.0% | 12.0% | 0% | 10.31 | 32.5 |
| 76 | 62.0% 57/38/5 | 8.0% | 18.0% | 12.0% | 0% | 11.15 | 24.9 |
| 77 | 64.0% 57/38/5 | 4.0% | 18.0% | 12.0% | 2.0% | 7.26 | 43.1 |

Examples 78–85

Copolymer (IOA/PyEA/MA 60/20/20, Example 2) was coated at a wet thickness of 15 mil (381 µm) onto a release liner. The coated liner was oven dried at 110° F. (43° C.) for 4 minutes, at 185° F. (85° C.) for 2 minutes and at 225° F. (107° C.) for 15 dried copolymer was stripped from the release liner and stored until used in formulating.

Dried copolymer (1.7501 g), terpineol (0.3864 g), tetraglycol (0.0089 g), testosterone (0.1693 g) and solvent (8.071 g of 90/10 ethyl acetate/methanol) were combined and mixed on a platform shaker until a homogeneous coating formulation was obtained. The formulation was coated at wet thickness of 29 mils (737 µm) onto a silicone release liner. The coated release liner was oven dried at 110° F. (43° C.) for 4 minutes, at 185° F. (85° C.) for 2 minutes, and at 225° F. (107° C.) for 2 minutes. Assuming that 61 percent of the terpineol and 16 percent of the tetraglycol were lost on drying, then the resulting pressure sensitive adhesive coating contained 7.0 percent terpineol, 3.5 percent tetraglycol, 7.9 percent testosterone, and 81.6 percent copolymer. The coated liner was then laminated to a 3 mil (76 µm) polyethylene backing.

Using the same copolymer and the same general method additional transdermal drug delivery devices were prepared. The weight percent of testosterone and the weight percent and identity of the excipients is shown in Table 9 below. The weight percentages assume that 61 percent of the terpineol, 16 percent of the tetraglycol and 13 percent of the lauryl glycol contained in the coating formulation were lost on drying.

The laminates were die cut into 2 cm² patches. The penetration through human cadaver skin and/or hairless mouse skin was determined using the test method described above. The receptor fluid was 30 percent N-methyl-2-pyrrolidone in water. Samples of receptor fluid were taken at 8, 16, 24, 48, 72 and 96 hours. The HPLC conditions were as follows: column: Supelcosil LC-18, 150×4.6 mm, 5 µm particle size; mobile phase: 60 percent deaerated water, 40 percent HPLC grade acetonitrile; flow rate: 2 mL/minute; detector: UV, 241 nm at 0.2 AUFS; run time: 5 minutes; injection volume: 20 µL. The cumulative flux and cumulative percent of drug penetrating for each time point are shown in Table 10 below where each value is the average of three independent determinations.

TABLE 9

IOA/PyEA/MA Copolymer Formulated with Testosterone

| Example Number | Testosterone | Terpineol | Tetraglycol | Lauryl Glycol | Lauramine Oxide |
|---|---|---|---|---|---|
| 78 | 7.9 | 7.0 | 3.5 | 0.0 | 0.0 |
| 79 | 7.3 | 5.3 | 3.0 | 2.6 | 0.0 |
| 80 | 5.9 | 0.0 | 5.3 | 5.5 | 0.0 |
| 81 | 9.4 | 6.9 | 3.5 | 0.0 | 0.0 |
| 82 | 8.8 | 5.2 | 2.6 | 2.6 | 0.0 |
| 83 | 7.4 | 0.0 | 5.3 | 5.3 | 0.0 |
| 84 | 7.1 | 5.1 | 2.6 | 2.7 | 3.4 |
| 85 | 5.7 | 0.0 | 5.2 | 5.0 | 3.5 |

TABLE 10

IOA/PyEA/MA Copolymer Formulated with Testosterone
In Vitro Human Cadaver Skin and Hairless Mouse Skin Penetration

| Example Number | Skin Type | Cumulative Flux (µg/cm²/hr) | | | | | | Cumulative Percent Drug Penetrating | | | | | |
|---|---|---|---|---|---|---|---|---|---|---|---|---|---|
| | | 8 hr | 16 hr | 24 hr | 48 hr | 72 hr | 96 hr | 8 hr | 16 hr | 24 hr | 48 hr | 72 hr | 96 hr |
| 78 | mouse | 1.06 | 2.05 | 2.76 | 3.52 | 3.45 | 3.12 | 2.20 | 8.47 | 17.1 | 43.7 | 64.0 | 77.1 |
| 79 | mouse | 3.22 | 6.33 | 8.76 | 9.76 | 8.44 | 7.12 | 3.32 | 13.1 | 27.3 | 60.9 | 79.0 | 88.9 |
| 79 | human | 1.39 | 1.90 | 2.22 | 2.44 | 2.20 | 1.86 | 1.65 | 4.50 | 7.89 | 17.4 | 23.4 | 26.3 |
| 80 | mouse | 3.30 | 4.93 | 5.40 | 4.14 | 3.15 | 2.52 | 13.1 | 39.1 | 64.2 | 98.6 | 112.9 | 120.4 |
| 81 | mouse | 2.65 | 3.47 | 3.79 | 3.68 | 3.24 | 2.84 | 5.69 | 14.8 | 24.3 | 46.9 | 61.9 | 72.5 |
| 82 | mouse | 2.76 | 4.80 | 6.08 | 6.63 | 5.73 | 4.84 | 4.31 | 15.0 | 28.4 | 62.0 | 80.6 | 90.9 |
| 82 | human | 4.85 | 5.17 | 4.99 | 3.91 | 2.95 | 2.36 | 8.03 | 16.9 | 24.3 | 37.6 | 42.4 | 45.3 |
| 83 | mouse | 3.61 | 6.24 | 7.56 | 7.49 | 6.26 | 5.19 | 6.25 | 21.5 | 39.0 | 77.0 | 96.5 | 106.6 |
| 84 | mouse | 4.97 | 9.13 | 10.49 | 8.94 | 6.79 | 5.36 | 8.60 | 31.6 | 54.7 | 93.8 | 107.0 | 112.6 |
| 84 | human | 4.03 | 4.99 | 5.12 | 4.43 | 3.45 | 2.77 | 6.82 | 16.8 | 25.9 | 44.7 | 52.1 | 55.9 |
| 85 | mouse | 3.86 | 7.88 | 9.80 | 8.24 | 6.14 | 4.81 | 7.50 | 30.6 | 56.9 | 95.3 | 106.5 | 111.3 |

Example 86

Isooctyl Acrylate/Pyrrolidonoethyl Acrylate/ Polymethyl Methacrylate Macromonomer (58/39/3; IV=0.92)

A masterbatch was prepared by combining polymethyl methacrylate macromonomer (36.48 g), ethyl acetate (1485 g), isooctyl acrylate (704.7 g), pyrrolidonoethyl acrylate (473.88 g), and 2,2'-azobis(2-methylbutyronitrile) (2.43 g) in a one gallon (3.8 L) glass bottle. The resulting solution was divided in equal portions and placed into six 1 quart (0.95 L) amber glass bottles. The bottles were deoxygenated by purging with nitrogen for 2 minutes. The bottles were sealed and placed in a rotating water bath at 57° C. for 24 hrs. At 24 hours the bottles were removed from the rotating water bath, unsealed, and recombined into a 1 gallon (3.8 L) glass jar. The percent solids of the resultant solution was 42.2%. The inherent viscosity was 0.92 dL/g.

Example 87

Isooctyl Acrylate/Pyrrolidonoethyl Acrylate/Vinyl Acetate/Polymethyl Methacrylate Macromonomer (62/15/20/3; IV=0.78)

A masterbatch was prepared by combining polymethyl methacrylate macromonomer (34.02 g), ethyl acetate (1519.02 g), methanol (44.28 g), isooctyl acrylate (703.08 g), pyrrolidonoethyl acrylate (170.1 g), vinyl acetate (226.8 g) and 2,2'-azobis(2-methylbutyronitrile) (2.268 g) in a one gallon (3.8 L) glass bottle. The resulting solution was divided in equal portions and placed into six 1 quart (0.95 L) amber glass bottles. The bottles were deoxygenated by purging with nitrogen for 2 minutes. The bottles were sealed and placed in a rotating water bath at 55° C. for 24 hrs. At 24 hours the bottles were removed from the rotating water bath, unsealed, and recombined into a 1 gallon (3.8 L) glass jar. The percent solids of the resultant solution was 37.4%. The inherent viscosity was 0.78 dL/g.

Example 88

Fentanyl (0.3703 g) was added to methanol (2.9937 g) and mixed until all of the fentanyl was dissolved. To this solution, copolymer (3.0446 g of dried Isooctyl Acrylate/ Pyrrolidonoethyl Acrylate/Polymethyl Methacrylate Macromonomer 58/39/3 IV=0.92, Example 86), methyl laurate (1.5005 g), and ethyl acetate (12.0089 g) were added and mixed until a uniform coating formulation was obtained. The coating formulation was knife coated at a wet thickness of 24 mil (609.6 μm) onto a release liner (Daubert 164P silicone coated release liner). The coated liner was oven dried for 4 minutes at 110° F. (43° C.), for 2 minutes at 185° F. (85° C.), and for 2 minutes at 225° F. (107° C.). The resulting coating contained 7.5 percent fentanyl and 30.5 percent methyl laurate. The coated liner was laminated onto a backing (SCOTCHPAK™ 1012 polyester film laminate; available from 3M Company). The permeation through human cadaver skin was determined using the test method described above. The results are shown in Table 12 below.

Examples 89–93

Using the general method of Example 88, a series of transdermal delivery devices in which the amount of fentanyl, the amount of softener, the choice of softener, and the copolymer were varied was prepared. The weight percent of fentanyl, weight percent softener, identity of softener, and identity of copolymer are given in Table 11 below. The balance of each formulation to 100 weight percent was copolymer. The abbreviations ML and IPM are used for methyl laurate and isopropyl myristate, respectively. The permeation through human cadaver skin was determined using the test method described above. The results are shown in Table 12 below.

TABLE 11

IOA/PyEA/VOAc/PMMAMac and IOA/PyEA/PMMAMac Copolymers Formulated with Fentanyl

| Example Number | Copolymer | IV (dL/g) | Fentanyl [%] | Softener |
|---|---|---|---|---|
| 88 | IOA/PyEA/PMMAMac 58/39/3 | 0.92 | 7.5 | 30.5% ML |
| 89 | IOA/PyEA/PMMAMac 58/39/3 | 0.92 | 7.0 | none |
| 90 | IOA/PyEA/PMMAMac 58/39/3 | 0.92 | 6.0 | 30.3% IPM |
| 91 | IOA/PyEA/VOAc/PMMAMac 63/15/20/2 | 0.78 | 7.0 | none |
| 92 | IOA/PyEA/VOAc/PMMAMac 62/15/20/3 | 0.78 | 7.4 | 30.5% ML |
| 93 | IOA/PyEA/VOAc/PMMAMac 63/15/20/2 | 0.78 | 6.0 | 29.9% IPM |

TABLE 12

Human Cadaver Skin Permeation

| Example Number | Average Cumulative Amount Penetrated (μg/cm²) | | | | | | | | | | |
|---|---|---|---|---|---|---|---|---|---|---|---|
| | 2 hr | 4 hr | 8 hr | 12 hr | 24 hr | 48 hr | 72 hr | 96 hr | 120 hr | 144 hr | 168 hr |
| 88 | 6.5 | 12 | 43 | 76 | 182 | 357 | 496 | 590 | 659 | 708 | 746 |
| 89 | 2.4 | 4.5 | 15 | 25 | 65 | 137 | 207 | 262 | 312 | 355 | 394 |
| 90 | 0.4 | 1.5 | 8.9 | 19 | 64 | 153 | 239 | 309 | 368 | 415 | 447 |
| 91 | 0.5 | 2.1 | 9.9 | 20 | 62 | 153 | 243 | 312 | 370 | 415 | 453 |
| 92 | 0.9 | 3.4 | 18 | 35 | 100 | 223 | 338 | 421 | 485 | 531 | 568 |
| 93 | 10 | 28 | 67 | 99 | 185 | 302 | 394 | 456 | 502 | 536 | 564 |

Example 94–97

Drug Solubility in IOA/PyEA (60/40) Pressure Sensitive Adhesive Copolymer

The solubility of several drugs in IOA/PyEA 60/40 pressure sensitive adhesive copolymer was determined using an accelerated method which is described in detail below. Drug solubility in an IOA pressure sensitive adhesive homopolymer was used for comparison purposes. The IOA/PyEA copolymer and the IOA homopolymer were both prepared using substantially the same method of preparation as for the copolymer prepared in Example 1.

In the accelerated drug solubility method, drug and pressure sensitive adhesive mixtures are made up over a wide range of drug concentrations and then these mixtures are seeded on their surface with pure drug crystal. If the crystals grow over time (typically one week) then the mixture is above the saturation concentration.

Separate stock solutions containing pressure sensitive adhesive in ethyl acetate and drug in a suitable solvent such as ethyl acetate or acetonitrile are prepared. The stock solutions are used to prepare 3 gram batches of drug and pressure sensitive adhesive solution. The amount of each stock solution needed is determined using the following equations, $$W_{DS} = \frac{3.0 \times C \times C_{PS}}{[C_{DS} \times (1 - C)] + (C_{PS} \times C)}$$

$$W_{PS} = \frac{3.0 \times C_{DS} \times (1 - C)}{[C_{DS} \times (1 - C)] + (C_{PS} \times C)}$$

where:

C is the desired concentration of drug in pressure sensitive adhesive after solvent removal;

$C_{DS}$ is the concentration of drug in the drug stock solution;

$C_{PS}$ is the concentration of pressure sensitive adhesive in the polymer stock solution;

$W_{DS}$ is the weight in grams of drug stock solution; and $W_{PS}$ is the weight in grams of pressure sensitive adhesive stock solution.

The calculated amounts of drug stock solution and pressure sensitive adhesive stock solution are combined in a glass vial. The vial is capped then shaken to provide a homogeneous solution.

Under a nitrogen atmosphere (e.g., in a glove box) individual drops of the drug and pressure sensitive adhesive solution are placed on a microscope slide and allowed to dry. Additional drops of solution are applied to each original spot until the spot is covered. The second application is allowed to dry. Applications are continued until a 2–3 mil (51–76 µm) layer has been built up. After the final application the slide is allowed to sit in the nitrogen atmosphere for at least 10 minutes.

The slide is removed from the nitrogen atmosphere and seeded with a very tiny amount of dry crystalline drug. A photomicrograph is taken to document the initial appearance of the crystalline "seeds". Periodically (e.g., daily or weekly) additional photomicrographs are taken and compared with earlier photomicrographs to determine if seed crystal growth or seed crystal absorption is occurring.

The results are usually reported as a range. The low value indicates the highest concentration sample where no crystal growth is observed. The high value indicates the lowest concentration where crystal growth is observed. In some instances additional work may be performed to narrow the range to a single value.

The solubilities of buprenorphine, cyproheptadine, phenobarbital and testosterone in both pure IOA and in IOA/ PyEA 60/40 were determined using this test method. The results are shown in Table 13 below.

TABLE 13

Drug Solubility in Pressure Sensitive Adhesive Copolymer (g drug/100 g pressure sensitive adhesive copolymer)

| Example Number | Drug | Copolymer | |
|---|---|---|---|
| | | IOA | IOA/PyEA 60/40 |
| 94 | Buprenorphine | 3.0–3.2 | 5–11 |
| 95 | Cyproheptadine | 5–6 | 10–15 |
| 96 | Phenobarbital | 3–4 | >15 |
| 97 | Testosterone | 0.5 | 4 |

Examples 98–99

The solubility of the drug lerisetron in two PSAs was determined by measurement of absorption of the drug into the pressure sensitive adhesive in a heterogeneous system. Lerisetron was dissolved in a receptor solution of HBSS buffer/ethanol (85:15 w:w) to give an initial concentration of 7.94 mg/10 mL. The 100% saturation concentration of lerisetron in the receptor solution is 9.93 mg/10 mL. A defined weight of pressure sensitive adhesive was added to 10 mL of receptor solution and the receptor solution was stirred for 4 hours. After the 4 hours of stirring, the concentration of lerisetron in the receptor solution was measured using standard HPLC techniques. The difference in the initial amount of lerisetron and the final amount of lerisetron in the solution is assumed to have been absorbed by the pressure sensitive adhesive. A partition coefficient between the receptor solution and pressure sensitive adhesive can be calculated. The solubility of lerisetron in the pressure sensitive adhesive can subsequently be determined based on the partition coefficient and the previously determined solubility of lerisetron in the receptor solution.

Lerisetron solubility in an Isooctyl Acrylate/ Pyrrolidonoethyl Acrylate/Polymethyl Methacrylate Macromonomer (59/39/2) was 7%. Lerisetron solubility in an Isooctyl Acrylate/Pyrrolidonoethyl Acrylate/Polymethyl Methacrylate Macromonomer (73/25/2) was 3%. A control pressure sensitive adhesive, Isooctyl Acrylate/N-vinyl pyrrolidone/Polymethyl Methacrylate Macromonomer (77/ 20/3) had a solubility of less than 1%.

Examples 100–103

Preparation of Copolymers of PYEA and IOA

Four copolymers were prepared by charging isooctyl acrylate (IOA), pyrrolidonoethyl acrylate (PyEA), 2,2'-azobis(2'methyl-butyronitrile), ethyl acetate, and methanol to a 125 gram glass bottle in the amounts shown in Table 12. The contents were deoxygenated by purging 35 seconds with nitrogen using a one liter per minute flow rate. The bottle was sealed and placed in a rotating water bath at 57° C. for 24 hours to effect essentially complete polymerization. The copolymer was optionally further diluted with ethyl acetate and methyl alcohol. The percent solids and the inherent viscosity was measured and the results are shown in Table 14 below.

TABLE 14

Preparation of IOA/PyEA Copolymers

| Ex. No. | Ratio of IOA/PyEA | IOA (grams) | PyEA (grams) | Initiator (grams) | Ethyl acetate/ methanol (grams) | Dilution ethyl acetate/ methanol (grams) | Percent Solids (%) | Inherent viscosity (g/dl) |
|---|---|---|---|---|---|---|---|---|
| 100 | 90/10 | 27 | 3 | 0.06 | 30.0/0.0 | 30.0/0.0 | 27.9 | 1.18 |
| 101 | 80/20 | 24 | 6 | 0.06 | 26.3/1.4 | 20.2/1.06 | 29.4 | 1.21 |
| 102 | 70/30 | 21 | 9 | 0.06 | 36.3/1.9 | 10.2/0.5 | 35.7 | 0.91 |
| 103 | 60/40 | 18 | 12 | 0.06 | 46.5/2.4 | 0.0/0.0 | 35.2 | 0.69 |

Examples 104–107

Two grams of iodine and 2.4 grams of sodium iodide were mixed in 10 ml of ethanol and added to the IOA/PyEA copolymers of examples 100 to 103 to obtain a formulation with weight percentages of: 2 percent iodine, 2.4 percent sodium iodide, and 95.6 percent IOA/PyEA copolymer.

The formulations were knife coated 15.24 cm (6 inches) wide and for approximately 122 cm (48 inches) using a 180 µm (7 mil) gap onto a silicon-coated paper release liner (available as a fully bleached Kraft paper coated on one side with polyethylene and overcoated with silicon (63 #1/00 4D/000) from Rexam Release, Bedford Park, Ill.). The liner was pulled through the coater at the rate of from 0.127 meters/second (m/s) to 0.254 m/s (5 to 10 inches per second). The coated formulations were allowed to evaporate for 2 minutes at ambient temperature, placed in a preheated vented convection oven at 87.8° C. (190° F.) for 4 minutes and allowed to cool to ambient temperature. The dry pressure sensitive adhesive coating thickness was from 25.4 µm to 50.8 µm (1–2 mil).

The coated pressure sensitive adhesives were laminated at 0.138 megapascal (Mpa) (20 pounds per square inch) at a speed of 5.08–20.54 cm/min (2–10 inches per minute) to a polyether-polyester film (commercially available as HYTREL™ polyester elastomer from E. I. du Pont deNemours and Company, Wilmington, Del.) to prepare a tape. The tape was placed in a sealed bag and gamma sterilized with a dose of 40 kiloGrays (kGy).

The time to complete kill, peel adhesion and launderability were measured using the test methods described above. The results of these tests are shown in Table 15 below.

TABLE 15

Antimicrobial Activity/Iodine Release, Peel Adhesion and Launderability

| Run Number | Length of Time for Complete Kill (hours) | Peel Adhesion (g/2.54 cm) (Method B) | Launderability PSA Release (Pass-Fail) | PSA Color Visibility (1–3) | PSA Residue after Peel (1–3) |
|---|---|---|---|---|---|
| 1 | 0.5 | 663 ± 3 | Fail | 2 | 3 |
| 2 | 1.0 | 1043 ± 242 | Fail | 3 | 3 |
| 3 | 2.0 | 889 ± 21 | Fail | 3 | 3 |
| 4 | 2.0 | 974 ± 21 | Fail | 3 | 3 |

Example 108

Isooctyl Acrylate/Pyrrolidonoethyl Methacrylate (60/40)

Isooctyl acrylate (120 g), pyrrolidonoethyl methacrylate (80 g), 2,2'-azobis(2-methlbutyronitrile) (0.3 g), ethyl acetate (194 g), and isopropyl alcohol (6 g) were added to a one liter glass bottle. The bottle was deoxygenated by purging with nitrogen at a one liter per minute flow rate for 2 minutes. The bottle was sealed and placed in a rotating water bath at 55° C. for 40 hours. The percent solids was measured at 45.8%. The inherent voscosity was 0.62 dL/g measured in ethyl acetate at 0.20 g/dL.

The present invention has been described with reference to several embodiments thereof. The foregoing detailed description and examples have been provided for clarity of understanding only, and no unnecessary limitations are to be understood therefrom. It will be apparent to those skilled in the art that many changes can be made to the described embodiments without departing from the spirit and scope of the invention. Thus, the scope of the invention should not be limited to the exact details of the compositions and structures described herein, but rather by the language of the claims that follow.

What is claimed is:

1. A pressure sensitive adhesive composition comprising a copolymer comprising
   (a) at least one A monomer selected from the group consisting of an alkyl acrylate containing 4 to 12 carbon atoms in the alkyl group and an alkyl methacrylate containing 4 to 12 carbon atoms in the alkyl group; and
   (b) pyrrolidonoethyl acrylate.

2. The composition of claim 1 wherein the A monomer is selected from the group consisting of isooctyl acrylate, 2-ethylhexyl acrylate, butyl acrylate, and cyclohexyl acrylate.

3. The composition of claim 1 wherein the A monomer is isooctyl acrylate.

4. The composition of claim 1 further comprising a B monomer that is copolymerizable with the A and pyrrolidoethyl acrylate.

5. The composition of claim 4 wherein the B monomer comprises a functional group selected from the group consisting of carboxylic acid, carboxylic acid ester, sulfonamide, urea, carbamate, carboxamide, hydroxy, amine, oxy, oxo, and cyano.

6. The composition of claim 1 wherein the copolymer further comprises a macromonomer.

7. The composition of claim 6 wherein the macromonomer is a functionally terminated polymethylmethacrylate.

8. The composition of claim 6 further comprising a drug in an amount such that the composition delivers a therapeutically effective amount for the indication being treated.

9. The composition of claim 8 wherein the copolymer contains from about 1% to about 6% of macromonomer by weight.

10. The composition of claim 9 wherein the copolymer contains from about 10% to about 45% of pyrrolidonoethyl acrylate by weight.

11. The composition of claim 10 wherein the copolymer further comprises vinyl acetate.

12. The composition of claim 10 further comprising a softener wherein the concentration of softener is from about 10% to about 40% based on the total weight of the composition.

13. The composition of claim 1 further comprising a drug in an amount such that the composition delivers a therapeutically effective amount for the indication being treated.

14. The composition of claim 1 further comprising a softener.

15. The composition of claim 14 wherein the softener is selected from the group consisting of a $C_8$–$C_{36}$ fatty acid; a $C_8$–$C_{36}$ fatty alcohol; a lower alkyl ester of a $C_8$–$C_{36}$ fatty acid; a di(lower) alkyl ester of a $C_6$–$C_8$ diacid; a monoglyceride of a $C_8$–$C_{36}$ fatty acid; tetraglycol; tetraethylene glycol; a $C_6$–$C_{36}$ alkyl pyrrolidone carboxylate; a polyethylene glycol; propylene glycol; 2-(2-ethoxyethoxy)ethanol; diethylene glycol monomethyl ether; N,N-dimethyldodecylamine N-oxide; and combinations of any two or more of the foregoing.

16. The composition of claim 14 wherein the concentration of softener is from about 10% to about 40% based on the total weight of the composition.

17. The composition of claim 1 further comprising an anti-microbial agent.

18. The composition of claim 17 wherein the anti-microbial agent is selected from the group consisting of chlorhexidine, a chlorhexidine salt, and mixtures thereof.

19. The composition of claim 17 wherein the anti-microbial agent is selected from the group consisting of iodine, iodine complexes with sodium or potassium iodide, and mixtures thereof.

20. The composition of claim 17 wherein the copolymer contains from about 5% to about 15% of pyrrolidonoethyl acrylate by weight.

21. The composition of claim 20 wherein the anti-microbial agent is selected from the group consisting of chlorhexidine, a chlorhexidine salt, and mixtures thereof.

22. The composition of claim 20 wherein the anti-microbial agent is selected from the group consisting of iodine, iodine complexes with sodium or potassium iodide, and mixtures thereof.

23. A transdermal delivery device comprising a backing and a composition according to claim 8, the composition being coated on at least a portion of a surface of the backing.

24. A transdermal drug delivery device comprising a backing and a composition according to claim 12, the composition being coated on at least a portion of a surface of the backing.

25. A transdermal drug delivery device comprising a backing and a composition according to claim 13, the composition being coated on at least a portion of a surface of the backing.

26. A method for transdermal delivery of a drug comprising the steps of (A) a step of providing a composition comprising
  (i) a copolymer comprising
    (a) at least one A monomer selected from the group consisting of an alkyl acrylate containing 4 to 12 carbon atoms in the alkyl group and an alkyl methacrylate containing 4 to 12 carbon atoms in the alkyl group; and
    (b) pyrrolidonoethyl acrylate; and
  (ii) a drug in an amount such that the composition delivers a therapeutically effective amount for the indication being treated; and (B) a step of applying the composition to an external part of the human body for a period sufficient to achieve the desired therapeutic result.

27. A pressure sensitive tape comprising a backing and a composition according to claim 1, the composition being coated on at least a portion of a surface of the backing.

28. A pressure sensitive adhesive copolymer comprising (a) at least one A monomer selected from the group consisting of an alkyl acrylate containing 4 to 12 carbon atoms in the alkyl group and an alkyl methacrylate containing 4 to 12 carbon atoms in the alkyl group; and (b) pyrrolidonoethyl acrylate.

29. The composition of claim 1 wherein the A monomer contains from about 40% to about 95% by weight.

* * * * *

UNITED STATES PATENT AND TRADEMARK OFFICE
CERTIFICATE OF CORRECTION

PATENT NO. : 6,902,740 B2
APPLICATION NO. : 09/901219
DATED : June 7, 2005
INVENTOR(S) : Mark S. Schaberg It is certified that error appears in the above-identified patent and that said Letters Patent is hereby corrected as shown below:

Column 3,
Line 44, delete "acetarnide" and insert in place thereof -- acetamide --.

Column 15,
Line 56, delete "I=0.61)" and insert in place thereof -- IV = 0.61) --.

Column 17,
Line 13, delete "Pyrrolidonoethvl" and insert in place thereof
　　-- Pyrrolidonoethyl --.
Line 56, delete "rminutes" and insert in place thereof -- minutes --.

Column 18,
Line 15, delete "V=1.08)" and insert in place thereof -- IV = 1.08) --.
Line 32, delete "I=0.95)" and insert in place thereof -- IV = 0.95) --.

Column 19,
Line 59, delete "V=0.52)" and insert in place thereof -- IV = 0.52) --.

Column 27,
Line 30, delete "methol" and insert in place thereof -- menthol --.

Column 29,
Line 20, delete "15" and insert in place thereof -- 15 minutes. The --.

Column 31,
Line 30, after "(2-methylobutyronitrile" insert -- ) --.

Column 34,
Line 53, delete "PYEA" and insert in place thereof -- PyEA --.

Column 35,
Line 67, delete "(2-methlbutyronitrile)" and insert in place thereof
　　-- (2-methylbutyronitrile) --.

Column 36,
Line 19, delete "voscosity" and insert in place thereof -- viscosity --.
Line 63, after "A" insert -- monomer --.
Line 63-64, delete "pyrrolidoethyl" and insert in place thereof
　　-- pyrrolidonoethyl --.

UNITED STATES PATENT AND TRADEMARK OFFICE
CERTIFICATE OF CORRECTION

PATENT NO. : 6,902,740 B2
APPLICATION NO. : 09/901219
DATED : June 7, 2005
INVENTOR(S) : Mark S. Schaberg It is certified that error appears in the above-identified patent and that said Letters Patent is hereby corrected as shown below:

Column 37,
Line 47, delete "potassium iodine," and insert in place thereof
-- potassium iodide, --.

Signed and Sealed this

Fifth Day of December, 2006

JON W. DUDAS
*Director of the United States Patent and Trademark Office*